United States Patent [19]

Warrellow et al.

[11] Patent Number: 5,580,888
[45] Date of Patent: Dec. 3, 1996

[54] STYRYL DERIVATIVES AS ANTI-INFLAMMATORY AGENTS

[75] Inventors: Graham J. Warrellow, Northwood; Ewan C. Boyd, Slough; Rikki P. Alexander, High Wycombe, all of United Kingdom

[73] Assignee: Celltech Therapeutics Limited, Berkshire, United Kingdom

[21] Appl. No.: 462,118

[22] Filed: Jun. 5, 1995

Related U.S. Application Data

[63] Continuation of Ser. No. 172,047, Dec. 22, 1993, abandoned.

[30] Foreign Application Priority Data

Dec. 23, 1992 [GB] United Kingdom ............. 9226830

[51] Int. Cl.$^6$ .................. A61K 31/44; C07D 401/10; C07D 405/10; C07D 409/10
[52] U.S. Cl. .............. 514/332; 514/252; 514/255; 514/256; 514/277; 514/292; 514/298; 514/306; 514/307; 514/311; 514/336; 514/338; 514/399; 546/81; 546/139; 546/152; 546/266; 546/339; 546/268.4; 546/269.1; 546/269.7; 546/270.1; 546/271.1; 546/271.4; 546/271.7; 546/272.1; 546/272.4; 546/272.7; 546/273.4; 546/275.1; 546/275.4; 546/276.4; 546/277.1; 546/277.4; 546/280.4; 546/281.1; 546/283.4; 546/284.1; 548/203; 548/206; 548/217; 548/235; 548/247; 548/252; 548/260; 548/267.8; 548/310.1; 548/341.1; 548/516; 549/58; 549/78; 549/471; 549/497; 568/631; 568/632
[58] Field of Search ................. 546/283, 81, 284, 546/101, 266, 139, 339, 152; 844/242, 180, 238, 335, 410; 548/341.1, 203, 206, 217, 235, 247, 252, 260, 267.8, 310.1, 516; 514/252, 341, 255, 342, 256, 343, 277, 292, 297, 298, 332, 335, 296, 307, 336, 338, 399, 311; 549/58, 78, 471, 497

[56] References Cited

U.S. PATENT DOCUMENTS

| | | | |
|---|---|---|---|
| 4,012,495 | 3/1977 | Schmiechen et al. | 548/543 |
| 4,015,017 | 3/1977 | Gazave | 424/331 |
| 4,153,713 | 5/1979 | Huth et al. | 548/543 |
| 4,193,926 | 3/1989 | Schmiechen et al. | 548/543 |
| 4,303,649 | 12/1981 | Jones | 424/177 |
| 4,792,561 | 12/1988 | Walker et al. | 514/312 |
| 4,921,862 | 5/1990 | Walker et al. | 514/312 |
| 4,971,959 | 11/1990 | Hawkins | 514/150 |
| 5,124,455 | 6/1992 | Lombardo | 546/181 |
| 5,128,358 | 7/1992 | Saccomano et al. | 514/392 |
| 5,175,167 | 12/1992 | Zipperer et al. | 514/277 |
| 5,177,085 | 1/1993 | Naef | 514/307 |
| 5,236,918 | 8/1993 | Amschler et al. | 514/247 |
| 5,274,002 | 12/1993 | Hawkins | 514/530 |
| 5,298,511 | 3/1994 | Waterson | 514/311 |
| 5,326,898 | 7/1994 | Chandraratna | 560/17 |

FOREIGN PATENT DOCUMENTS

| | | |
|---|---|---|
| 0393500 | 10/1990 | European Pat. Off. . |
| 0490823 | 6/1991 | European Pat. Off. . |
| 0470805 | 2/1992 | European Pat. Off. . |
| 0511865 | 11/1992 | European Pat. Off. . |
| 0537742 | 4/1993 | European Pat. Off. . |
| 2501443 | 7/1975 | Germany . |
| 1588639 | 4/1981 | United Kingdom . |
| WO87/06576 | 11/1987 | WIPO . |
| WO91/15451 | 10/1991 | WIPO . |
| WO91/16892 | 11/1991 | WIPO . |
| WO92/00968 | 1/1992 | WIPO . |
| WO92/06963 | 4/1992 | WIPO . |
| WO92/06085 | 4/1992 | WIPO . |
| WO92/07567 | 5/1992 | WIPO . |
| WO92/19594 | 11/1992 | WIPO . |
| WO92/19602 | 11/1992 | WIPO . |
| WO93/19748 | 10/1993 | WIPO . |
| WO94/02465 | 2/1994 | WIPO . |
| WO94/12461 | 6/1994 | WIPO . |

OTHER PUBLICATIONS

Ashton, "Selective Type IV Phosphodiesterase Inhibitors as Antiasthmatic Agents. The Syntheses and Biological Activities of 3-(Cyclopentyloxy)-4-methyoxybenzamides and Analogues" J. Med. Chem. 37: 1696–1703 (1994).

Buu–Hoi, N. P. et al., "Bromination of Some 1,2,2-Triarylethylenes" 1261–1263 (1958).

Buu–Hoi et al., "New Method for the Synthesis of ω,ω-Diarylacetophenones Aminated in the Aromatic Nucleus. Plynitration of Triarylethylenes" Chemical Abstracts 61: 16006h (1964).

(List continued on next page.)

Primary Examiner—Ceila Chang
Attorney, Agent, or Firm—Woodcock Washburn Kurtz MacKiewicz & Norris

[57] ABSTRACT

Compounds of general formula (1)

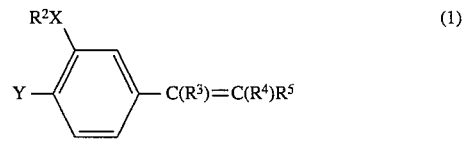

are described wherein Y is a halogen atom or a group —$OR^1$, wherein $R^1$ is an optionally substituted alkyl group; X is —O—, —S— or —N($R^6$)—, where $R^6$ is a hydrogen atom or an alkyl group; $R^2$ is an optionally substituted alkyl, alkenyl, cycloalkyl or cycloalkenyl group; $R^3$ and $R^4$, which may be the same or different, is each a group —$(CH^2)_n$Ar, where Ar is a monocyclic or bicyclic aryl group optionally containing one or more heteroatoms selected from oxygen, sulphur or nitrogen atoms and n is zero or an integer 1, 2 or 3; $R^5$ is a hydrogen atom or an optionally substituted alkyl group; and the salts, solvates, hydrates and N-oxides. Compounds according to the invention are potent, selective and orally active PDE IV inhibitors and are useful in the prophylaxis and treatment of asthma.

14 Claims, No Drawings

OTHER PUBLICATIONS

Chemical Abstracts. Registry Handbook–Number Section. Printed Issues Columbus US *compounds with registry numbers 95992–21–5; 95971–60–1; 90053–37–5; 82668–18–6; 80395–25–1; 49610–49–3 (1982).

El–Wakil et al., "Study of the proton magnetic resonance of methoxytamoxifen towards ortho–substitiution" Chemical Abstracts 116: 255248t (1992).

Hirose et al., "Styrene Derivatives and Electrophotpgraphic Photoreceptor Containing Them" Chemical Abstracts 118: 136183z (1993).

Manhas et al., "heterocyclic Compounds XII. Quinazoline Derivatives as Potential Antifertility Agents (1)" J. Het Chem: 711–715 (1979).

Mezheritskaya, "Synthesis and properties of carboxonium het=erocyclic systems. VII. Synthesis and properties of 2–benzyl–substituted 1,3–dioxolanium salts" Chem. Abs. 93: 95160j p. 635 (1980).

O'Conner et al., "Voltammetry and Controlled Potential Oxidation of 3,4–dimethoxypropenylbenzene at a rotating platinum electrode in unbuffered acetonitrile and in acetonitrile–pyridine solution" Chemical Abstracts 60(8) #10203.4 (Apr. 13, 1964).

Ramalingam, Deshmukh and Sattur, "Synthesis and Pharmacology of 2,5–Disubstituted 1,3,4–Zxadiazoles" J. Indian Chem. Soc. vol. 58(3) 269–271 (1981).

Reddy et al., "Inhibition of Breast Cancer Cell Growth in Vitro by a Tyrosine Kinase Inhibitor" Cancer Research 52: 3636–3641 (1992).

Schneider et al "Catechol Estrogens of the 1,1, 2–triphenyl–but–1–ene Type." J. Med. 29 Chem. 1355–1362 (1986).

Schneider et al., "Catechol Estrogens of the 1,1, 2–Triphenylbut–1–ene Type: Relationship Between Structure, Estradiol Receptor Affinity, Estrogenic and Antiestrogenic Properties, and Mammary Tumor Inhibiting Activities" J. Med. Chem. 29: 1355–1362 (1986).

Seitz et al., "Fluorotamoxifen. A Caveat on the Generality of Electrophilic Destannylation" Chemical Abstracts 111: 57136k 57133k (1989).

Yoneda et al., "The Antiproliferative Effects of Tyrosine Kinase Inhibitors Tyrphostins on a Human Squamous Cell Carcinoma in Vitro and in Nude Mice" Cancer Research 51: 4430–4435 (1991).

Beavo, et al. " Primary Sequence Of Cyclie Nucleotide Phosphodiesterase Isozymes And The Design Of Selective Inhibitors", *TIPS* 11:150–155 (1990).

Nicholson, et al. "Differential Modulation Of Tissue Function And Therapeutic Potential Of Selective Inhibitors Of Cyclic Nucleotide Phosphodiesterase Isoenzymes", *TIPS* 12:19–27 (1991).

Meyers, et al., "Oxazolines. XI. Synthesis Of Functionalized Aromatic And Aliphatic Acids. A Useful Protecting Group For Carboxylic Acids Against Grignard And Hydride Reagents", *J. Org. Chem.*, vol. 39:2787 (1974).

Livi, et al., "Cloning And Expression Of cDNA For A Human Low–$K_{m3}$ Rolipram–Sensitive Cyclic AMP Phosphodiesterase", *Molecular and Cellular Biology*, 10:2678 (1990).

Yeadon, et al., "Mechanisms Contributing To Ozone–Induced Bronchial Hyperreactivity In Guinea–Pigs", *Pulmonary Pharm.* 5:39 (1992).

STYRYL DERIVATIVES AS ANTI-INFLAMMATORY AGENTS

This is a continuation of U.S. application Ser. No. 08/172,047, filed Dec. 22, 1993, abandoned.

This invention relates to a novel series of styryl derivatives, to processes for their preparation, to pharmaceutical compositions containing them, and to their use in medicine.

Many hormones and neurotransmitters modulate tissue function by elevating intra-cellular levels of adenosine 3', 5'-cyclic monophosphate (cAMP). The cellular levels of cAMP are regulated by mechanisms which control synthesis and breakdown. The synthesis of cAMP is controlled by adenylyl cyclase which may be directly activated by agents such as forskolin or indirectly activated by the binding of specific agonists to cell surface receptors which are coupled to adenylyl cyclase. The breakdown of cAMP is controlled by a family of phosphodiesterase (PDE) isoenzymes, which also control the breakdown of guanosine 3',5'-cyclic monophosphate (cGMP). To date, seven members of the family have been described (PDE I–VII) the distribution of which varies from tissue to tissue. This suggests that specific inhibitors of PDE isoenzymes could achieve differential elevation of cAMP in different tissues, [for reviews of PDE distribution, structure, function and regulation, see Beavo & Reifsnyder (1990) TIPS, 11:150–155 and Nicholson et al (1991) TIPS, 12: 19–27].

There is clear evidence that elevation of cAMP in inflammatory leukocytes leads to inhibition of their activation. Furthermore, elevation of cAMP in airway smooth muscle has a spasmolytic effect. In these tissues, PDE IV plays a major role in the hydrolysis of cAMP. It can be expected, therefore, that selective inhibitors of PDE IV would have therapeutic effects in inflammatory diseases such as asthma, by achieving both antiinflammatory and bronchodilator effects.

The design of PDE IV inhibitors has met with limited success to date, in that many of the potential PDE IV inhibitors which have been synthesised have lacked potency and/or have been capable of inhibiting more than one type of PDE isoenzyme in a non-selective manner. Lack of a selective action has been a particular problem given the widespread role of cAMP in vivo and what is needed are potent selective PDE IV inhibitors with an inhibitory action against PDE IV and little or no action against other PDE isoenzymes.

We have now found a novel series of styryl derivatives, members of which compared to known structurally similar compounds are potent inhibitors of PDE IV at concentrations at which they have little or no inhibitory action on other PDE isoenzymes. These compounds inhibit the isolated PDE IV enzyme and also elevate cAMP in isolated leukocytes. Certain compounds prevent inflammation in the lungs induced by carrageenan, platelet-activating factor (PAF), interleukin-5 (IL-5) or antigen challenge. These compounds also suppress the hyperresponsiveness of airway smooth muscle seen in inflamed lungs. Advantageously, compounds according to the invention have good oral activity and at orally effective doses exhibit little or none of the side-effects associated with known PDE IV inhibitors, such as rolipram. The compounds of the invention are therefore of use in medicine, especially in the prophylaxis and treatment of asthma.

Thus according to one aspect of the invention, we provide a compound of formula (1)

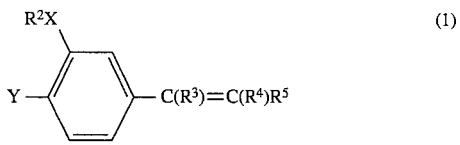

wherein
Y is a halogen atom or a group —$OR^1$, where $R^1$ is an optionally substituted alkyl group;

X is —O—, —S— or —$N(R^6)$—, where $R^6$ is a hydrogen atom or an alkyl group.

$R^2$ is an optionally substituted alkyl, alkenyl, cycloalkyl or cycloalkenyl group;

$R^3$ and $R^4$, which may be the same or different, is each a group —$(CH_2)_n Ar$, where Ar is a monocyclic or bicylic aryl group optionally containing one or more heteroatoms selected from oxygen, sulphur or nitrogen atoms and n is zero or an integer 1, 2 or 3;

$R^5$ is a hydrogen atom or an optionally substituted alkyl group; and the salts, solvates, hydrates and N-oxides thereof.

The compounds of formula (1) exist as geometrical isomers and the invention extends to all such individual isomers and mixtures thereof. Formula (1) and the formulae hereinafter should be understood to include all individual isomers and mixtures thereof, unless stated otherwise, and even though only one isomer may be depicted.

In the compounds of formula (1), when Y is a halogen atom it may be for example a fluorine, chlorine, bromine or iodine atom.

When Y in the compounds of formula (1) is a group —$OR^1$, $R^1$ may be, for example, an optionally substituted straight or branched alkyl group, for example, an optionally substituted $C_{1-6}$alkyl group, such as a methyl, ethyl, n-propyl, or i-propyl, group. Optional substituents which may be present on $R^1$ groups include one or more halogen atoms, e.g. fluorine, or chlorine atoms. Particular substituted alkyl groups include for example —$CH_2F$, —$CH_2Cl$, —$CHF_2$, —$CHCl_2$, —$CF_3$ or —$CCl_3$ groups.

Alkyl groups represented by $R^2$ or $R^5$ in the compounds of formula (1) include optionally substituted straight or branched $C_{1-6}$ alkyl groups, e.g. $C_{1-3}$ alkyl groups such as methyl or ethyl groups. Optional substituents on these groups include one, two or three substituents selected from halogen atoms, e.g. fluorine, chlorine, bromine or iodine atoms, or hydroxyl or $C_{1-6}$ alkoxy e.g. $C_{1-3}$ alkoxy such as methoxy or ethoxy groups.

Alkenyl groups represented by $R^2$ in the compounds of formula (1) include optionally substituted straight or branched $C_{2-6}$alkenyl groups such as ethenyl, propen-1-yl and 2-methylpropen-1-yl. Optional substituents include those described above in relation to the groups $R^2$ and $R^5$.

When $R^2$ in the compounds of formula (1) is an optionally substituted cycloalkyl or cycloalkenyl group it may be for example a $C_{3-8}$cycloalkyl group such as a cyclobutyl, cyclopentyl or cyclohexyl group or a $C_{3-8}$cycloalkenyl group containing for example one or two double bonds such as 2-cyclobuten-1-yl, 2-cyclopenten-1-yl, 3-cyclopenten-1-yl, 2,4-cyclopentadien-1-yl, 2-cyclohexen-1-yl, 3-cyclohexen-1-yl, 2,4-cyclohexadien-1-yl or 3,5-cyclohexadien-1-yl group, each cycloalkyl or cycloalkenyl group being optionally substituted by one, two or three substituents selected from halogen atoms, e.g. fluorine, chlorine, bromine or iodine atoms, straight or branched $C_{1-6}$alkyl e.g. $C_{1-3}$alkyl such as methyl or ethyl, hydroxyl or $C_{1-6}$alkoxy e.g. $C_{1-3}$alkoxy such as methoxy or ethoxy groups.

Alkyl groups represented by $R^6$ in compounds of formula (1) include straight or branched $C_{1-6}$ alkyl groups, e.g. $C_{1-3}$ alkyl groups such as methyl or ethyl groups.

In the compounds of formula (1) the groups $R^3$ and/or $R^4$ may each independently be a group —Ar, —CH$_2$Ar, —(CH$_2$)$_2$Ar or —(CH$_2$)$_3$Ar.

Monocyclic or bicyclic aryl groups represented by the group Ar in compounds of formula (1) include for example $C_{6-12}$ optionally substituted aryl groups, for example optionally substituted phenyl, 1- or 2-naphthyl, indenyl or isoindenyl groups.

When the monocyclic or bicyclic aryl group Ar contains one or more heteroatoms it may be for example a $C_{1-9}$ optionally substituted heteroaryl group containing for example one, two, three or four heteroatoms selected from oxygen, sulphur or nitrogen atoms. In general, Ar heteroaryl groups may be for example monocyclic or bicyclic heteroaryl groups. Monocyclic heteroaryl groups include for example five- or six-membered heteroaryl groups containing one, two, three or four heteroatoms selected from oxygen, sulphur or nitrogen atoms.

Examples of heteroaryl groups represented by Ar include pyrrolyl, furyl, thienyl, imidazolyl, N-methylimidazolyl, N-ethylimidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, pyridyl, pyrimidinyl, pyridazinyl, pyrazinyl, 1,3,5-triazinyl, 1,2,4-triazinyl, 1,2,3-triazinyl, benzofuryl, isobenzofuryl, benzothienyl, isobenzothienyl, indolyl, isoindolyl, benzimidazolyl, benzothiazolyl, benzoxazolyl, quinazolinyl, naphthyridinyl, pyrido[3,4-b]pyridyl, pyrido[3,2-b]pyridyl, pyrido[4,3-b]pyridyl, quinolinyl, isoquinolinyl, tetrazolyl, 5,6,7,8-tetrahydroquinolinyl and 5,6,7,8-tetrahydroisoquinolinyl.

The heteroaryl group represented by Ar may be attached to the remainder of the molecule of formula (1) through any ring carbon or heteroatom as appropriate. Thus, for example, when the group Ar is a pyridyl group it may be a 2-pyridyl, 3-pyridyl or 4-pyridyl group. When it is a thienyl group it may be a 2-thienyl or 3-thienyl group, and, similarly, when it is a furyl group it may be a 2-furyl or 3-furyl group.

When in compounds of formula (1) the Ar group is a nitrogen-containing heterocycle it may be possible to form quaternary salts, for example N-alkyl quaternary salts and the invention is to be understood to extend to such salts. Thus for example when the group Ar is a pyridyl group, pyridinium salts may be formed, for example N-alkylpyridinium salts such as N-methylpyridinium.

The aryl or heteroaryl groups represented by Ar in compounds of formula (1) may each optionally be substituted by one, two, three or more substituents [$R^7$]. The substituent $R^7$ may be selected from an atom or group $R^8$ or —Alk$^1$ ($R^8$)$_m$ wherein $R^8$ is a halogen atom, or an amino (—NH$_2$), substituted amino, nitro, cyano, hydroxyl (—OH), substituted hydroxyl, cycloalkoxy, formyl [HC(O)—], carboxyl (—CO$_2$H), esterified carboxyl, thiol (—SH), substituted thiol, —C(O)Alk$^1$, —SO$_3$H, —SO$_2$Alk$^1$, —SO$_2$NH$_2$13 SO$_2$NHAlk$^1$, —SO$_2$N[Alk$^1$]$_2$, —CONH$_2$, —CONHAlk$^1$, C—ON[Alk$^1$]$_2$, —NHSO$_2$H, —NHSO$_2$Alk$^1$, —N[SO$_2$Alk$^1$]$_2$, —NHSO$_2$NH$_2$, —NHSO$_2$NHAlk$^1$, —NHSO$_2$N[Alk$^1$]$_2$, —NHC(O)Alk$^1$, or —NHC(O)OAlk$^1$ group; Alk$^1$ is a straight or branched $C_{1-6}$alkylene, $C_{2-6}$alkenylene, or $C_{2-6}$alkynylene chain optionally interrupted by one, two, or three —O—, or —S— atoms or —S(O)p—, [where p is an integer 1 or 2] or —N(R$^6$)— groups; and m is zero or an integer 1, 2 or 3.

When in the group —Alk$^1$ ($R^8$)$_m$ m is an integer 1, 2 or 3, it is to be understood that the substituent or substituents $R^8$ may be present on any suitable carbon atom in —Alk$^1$. Where more than one $R^8$ substitutent is present these may be the same or different and may be present on the same or different carbon atom in Alk$^1$. Clearly, when m is zero and no substituent $R^8$ is present or when Alk$^1$ forms part of a group such as —SO$_2$Alk$^1$ the alkylene, alkenylene or alkynylene chain represented by Alk$^1$ becomes an alkyl, alkenyl or alkynyl group.

When $R^8$ is a substituted amino group it may be a group —NH[Alk$^1$(R$^{8a}$)$_m$] [where Alk$^1$ and m are as defined above and $R^{8a}$ is as defined above for $R^8$ but is not a substituted amino, a substituted hydroxyl or a substituted thiol group] or a group —N[Alk$^1$ (R$^{8a}$)$_m$]$_2$ wherein each —Alk$^1$(R$^{8a}$)$_m$ group is the same or different.

When $R^8$ is a halogen atom it may be for example a fluorine, chlorine, bromine, or iodine atom.

When $R^8$ is a cycloalkoxy group it may be for example a $C_{5-7}$cycloalkoxy group such as a cyclopentyloxy or cyclohexyloxy group.

When $R^8$ is a substituted hydroxyl or substituted thiol group it may be a group —OAlk$^1$(R$^{8a}$)$_m$ or —SAlk$^1$(R$^{8a}$)$_m$ respectively, where Alk$^1$, $R^{8a}$ and m are as just defined.

Esterified carboxyl groups represented by the group $R^8$ include groups of formula —CO$_2$Alk$^2$ wherein Alk$^2$ is a straight or branched, optionally substituted $C_{1-8}$alkyl group such as a methyl, ethyl, n-propyl, i-propyl, n-butyl, i-butyl, s-butyl or t-butyl group; a $C_{6-12}$aryl$C_{1-8}$alkyl group such as an optionally substituted benzyl, phenylethyl, phenylpropyl, 1-naphthylmethyl or 2-naphthylmethyl group; a $C_{6-12}$aryl group such as an optionally substituted phenyl, 1-naphthyl or 2-naphthyl group; a $C_{6-12}$aryloxy$C_{1-8}$alkyl group such as an optionally substituted phenyloxymethyl, phenyloxyethyl, 1-naphthyloxymethyl, or 2-naphthyloxymethyl group; an optionally substituted $C_{1-8}$alkanoyloxy$C_{1-8}$alkyl group, such as a pivaloyloxymethyl, propionyloxyethyl or propionyloxypropyl group; or a $C_{6-12}$aroyloxy$C_{1-8}$alkyl group such as an optionally substituted benzoyloxyethyl or benzoyloxypropyl group. Optional substituents present on the Alk$^2$ group include $R^7$ substituents described above.

When Alk$^1$ is present in or as a substituent $R^7$ it may be for example a methylene, ethylene, n-propylene, i-propylene, n-butylene, i-butylene, s-butylene, t-butylene, ethenylene, 2-propenylene, 2-butenylene, 3-butenylene, ethynylene, 2-propynylene, 2-butynylene or 3-butynylene chain, optionally interrupted by one, two, or three —O— or —S—, atoms or —S(O)—, —S(O)$_2$— or —N(R$^6$)— groups.

Particularly useful atoms or groups represented by $R^7$ include fluorine, chlorine, bromine or iodine atoms, or $C_{1-6}$alkyl, e.g. methyl or ethyl, $_6$alkylamino, e.g. methylamino or ethylamino, $C_{1-6}$ hydroxyalkyl, e.g. hydroxymethyl or hydroxyethyl, $C_{1-6}$alkylthiol e.g. methylthiol or ethylthiol, $C_{1-6}$alkoxy, e.g. methoxy or ethoxy, $C_{5-7}$cycloalkoxy, e.g. cyclopentyloxy, halo$C_{1-6}$alkyl, e.g. trifluoromethyl, $C_{1-6}$alkylamino, e.g. methylamino or ethylamino, amino (—NH$_2$), amino$C_{1-6}$alkyl, e.g. aminomethyl or aminoethyl, $C_{1-6}$dialkylamino, e.g. dimethylamino or diethylamino, nitro, cyano, hydroxyl (—OH), formyl [HC(O)—], carboxyl (—CO$_2$H), —CO$_2$Alk$^2$ [where Alk$^2$ is as defined above], $C_{1-6}$ alkanoyl e.g. acetyl, thiol (—SH), thio$C_{1-6}$alkyl, e.g. thiomethyl or thioethyl, sulphonyl (—SO$_3$H), $C_{1-6}$alkylsulphonyl, e.g. methylsulphonyl, aminosulphonyl (—SO$_2$NH$_2$), $C_{1-6}$alkylaminosulphonyl, e.g. methylaminosulphonyl or ethylaminosulphonyl, $C_{1-6}$dialkylaminosulphonyl, e.g. di-methylaminosulphonyl or diethylaminosulphonyl, carboxamido (—CONH$_2$), $C_{1-6}$alkylaminocarbonyl, e.g. methylaminocarbonyl or ethylaminocarbonyl, $C_{1-6}$dialkylaminocarbonyl, e.g. dimethylaminocarbonyl or diethylaminocarbonyl, sulphonylamino (—$NHSO_2H$), $C_{1-6}$alkylsulphonylamino, e.g. methylsulphonylamino or ethylsulphonylamino, $C_{1-6}$dialkylsulphonylamino, e.g. dimethylsulphonylamino or diethylsulphonylamino, aminosulphonylamino (—$NHSO_2NH_2$), $C_{1-6}$alkylaminosulphonylamino, e.g. methylaminosulphonylamino or ethylaminosulphonylamino, $C_{1-6}$dialkylaminosulphonylamino, e.g. dimethylaminosulphonylamino or diethylaminosulphonylamino, $C_{1-6}$alkanoylamino, e.g. acetylamino, $C_{1-6}$alkanoylamino $C_{1-6}$alkyl, e.g. acetylaminomethyl or $C_{1-6}$alkoxycarbonylamino, e.g. methoxycarbonylamino, ethoxycarbonylamino or t-butoxycarbonylamino groups.

Where desired, two $R^7$ substituents may be linked together to form a cyclic group such as a cyclic ether, e.g. a $C_{2-6}$alkylenedioxy group such as ethylenedioxy.

It will be appreciated that where two or more $R^7$ substituents are present, these need not necessarily be the same atoms and/or groups. The $R^7$ substituents may be present at any ring carbon atom away from that attached to the rest of the molecule of formula (1). Thus, for example, in phenyl groups represented by Ar any substituent may be present at the 2-, 3-, 4-, 5- or 6-positions relative to the ring carbon atom attached to the remainder of the molecule.

In the compounds of formula (1), when an ester group is present, for example a group —$CO_2Alk^2$ this may advantageously be a metabolically labile ester.

The presence of certain substituents in the compounds of formula (1) may enable salts of the compounds to be formed. Suitable salts include pharmaceutically acceptable salts, for example acid addition salts derived from inorganic or organic acids, and salts derived from inorganic and organic bases.

Acid addition salts include hydrochlorides, hydrobromides, hydroiodides, alkylsulphonates, e.g. methanesulphonates, ethanesulphonates, or isethionates, arylsulphonates, e.g. p-toluenesulphonates, besylates or napsylates, phosphates, sulphates, acetates, trifluoroacetates, propionates, citrates, maleates, fumarates, malonates, succinates, lactates, oxalates, tartrates and benzoates.

Salts derived from inorganic or organic bases include alkali metal salts such as sodium or potassium salts, alkaline earth metal salts such as magnesium or calcium salts, and organic amine salts such as morpholine, piperidine, dimethylamine or diethylamine salts.

Particularly useful salts of compounds according to the invention include pharmaceutically acceptable salts, especially acid addition pharmaceutically acceptable salts.

In the compounds of formula (1), the group Y is preferably an —$OR^1$ group, especially where $R^1$ is an optionally substituted ethyl group or, especially, an optionally substituted methyl group. Especially useful substitutents which may be present on $R^1$ groups include one, two or three fluorine or chlorine atoms.

The group X in compounds of formula (1) is preferably —O—.

A particularly useful group of compounds of formula (1) has the formula (2):

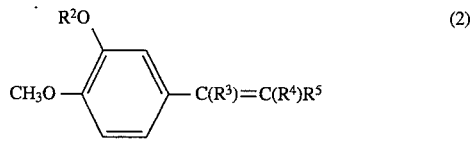
(2)

where $R^2$ is an optionally substituted cycloalkyl group; $R^3$, $R^4$, and $R^5$ are as defined for formula (1); and the salts, solvates, hydrates and N-oxides thereof.

In the compounds of formulae (1) or (2) $R^2$ is preferably an optionally substituted cyclopentyl group. In particular, $R^2$ is a cyclopentyl group.

In compounds of formulae (1) or (2) the group $R^5$ is preferably a hydrogen atom.

The group $R^3$ and $R^4$ in compounds of formulae (1) or (2) is each preferably a —$CH_2Ar$ group, or, especially an —Ar group.

Particularly useful $R^3$ or $R^4$ groups in compounds of formulae (1) or (2) include those $R^3$ or $R^4$ groups in which Ar is a monocyclic aryl group optionally containing one or more heteroatoms selected from oxygen, sulphur, or, in particular, nitrogen atoms, and optionally substituted by one, two or more $R^7$ substituents. In these compounds, when the group represented by Ar is a heteroaryl group it is preferably a nitrogen-containing monocyclic heteroaryl group, especially a six-membered nitrogen-containing heteroaryl group. Thus, in one preferred example, the groups $R^4$ and $R^5$ may each be a six-membered nitrogen-containing heteroaryl group. In another preferred example $R^4$ may be a monocyclic aryl group and $R^5$ may be a six-membered nitrogen-containing heteroaryl group. In these examples, the six-membered nitrogen-containing heteroaryl group may be an optionally substituted pyridyl, pyridazinyl, pyrimidinyl or pyrazinyl group. Particular examples include optionally substituted 2-pyridyl, 3-pyridyl or, especially, 4-pyridyl, 3-pyridazinyl, 4-pyridazinyl, 5-pyridazinyl, 2-pyrimidinyl, 4-pyrimidinyl, 5-pyrimidinyl, 2-pyrazinyl or 3-pyrazinyl. The monocyclic aryl group may be a phenyl group or a substituted phenyl group.

One particularly useful group of compounds of formulae (1) or (2) is that wherein $R^3$ and $R^4$ is each a pyridyl or, especially, a monosubstituted pyridyl, or preferably a disubstituted pyridyl group, or $R^3$ is a phenyl or substituted phenyl group and $R^4$ is a pyridyl or, especially a monosubstituted pyridyl, or preferably a disubstituted pyridyl group.

In this particular group of compounds and also in general in compounds of formulae (1) or (2), when $R^3$ and/or $R^4$ is a substituted phenyl group it may be for example a mono-, di- or trisubstituted phenyl group in which the substituent is an atom or group $R^7$ as defined above. When the $R^3$ and/or $R^4$ group is a monosubstituted phenyl group the substituent may be in the 2-, or preferably 3-, or especially 4-position relative to the ring carbon atom attached to the remainder of the molecule.

When in compounds of formulae (1) or (2) $R^3$ and/or $R^4$ is a substituted pyridyl group it may be for example a mono-or disubstituted pyridyl group, such as a mono- or disubstituted 2-pyridyl, 3-pyridyl or especially 4-pyridyl group substituted by one or two atoms or groups $R^7$ as defined above, in particular one or two halogen atoms such as fluorine or chlorine atoms, or methyl, methoxy, hydroxyl or nitro groups. Particularly useful pyridyl groups of these types are 3-monosubstituted-4-pyridyl or 3,5-disubstituted-4-pyridyl, or 2- or 4-monosubstituted-3-pyridyl or 2,4-disubstituted-3-pyridyl groups.

A particularly useful group of compounds according to the invention has the formula (2) wherein $R^5$ is a hydrogen atom and $R^3$ and $R^4$ are as defined for formula (1); and the salts, solvates, hydrates and N-oxides thereof. Compounds of this type in which $R^3$ is an optionally substituted phenyl, or pyridyl in particular 4-pyridyl, group and $R^4$ is a pyridyl especially a 4-pyridyl group are particularly preferred.

Particularly useful compounds according to the invention are the (E) and (Z) isomers of
4-[2-(3-Cyclopentyloxy-4-methoxyphenyl)-2-(2-furanyl)ethenyl]pyridine;
4-[2-(3-Cyclopentyloxy-4-methoxyphenyl)-2-(2thienyl)ethenyl]pyridine;
4-[2-(3-Cyclopentyloxy-4-methoxyphenyl)-2-phenylethenyl]-3-methylimidazole;

4-[2-(3-Cyclopentyloxy-4-methoxyphenyl)-2-phenylethenyl]pyridine;
4-[1-(3-Cyclopentyloxy-4-methoxyphenyl)-2-(4-pyridyl)ethenyl]pyridine;
4-[2-(3-Cyclopentyloxy-4-methoxyphenyl)-2-(4-fluorophenylethenyl]pyridine;
4-[2-(3-Cyclopentyloxy-4-methoxyphenyl)-2-(4-trifluoromethylphenyl)ethenyl]pyridine;
4-[2-(3-Cyclopentyloxy-4-methoxyphenyl)-2-(2-methoxyphenylethenyl)]pyridine;
4-[2-(3-Cyclopentyloxy-4-methoxyphenyl)-2-( 4-methoxyphenyl)ethenyl]pyridine;
4-[2-(3-Cyclopentyloxy-4-methoxyphenyl)-2-(4-methylphenyl) ethenyl]pyridine;
4-[2-(3-Cyclopentyloxy-4-methoxyphenyl)-2-(3-methylphenyl)ethenyl]pyridine;
4-[2-(3-Cyclopentyloxy-4-methoxyphenyl)-2-(3-cyclopentyloxy-4-methoxyphenyl)ethenyl]pyridine;
4-[2-(3-Cyclopentyloxy-4-methoxyphenyl)-2-phenylethenyl]-3,5-dichloropyridine;
2-[2-(3-Cyclopentyloxy-4-methoxyphenyl)-2-phenylethenyl]pyridine;
4-[1-(3-Cyclopentyloxy-4-methoxyphenyl)-2-(4-pyridyl)ethenyl]aniline;
4-[1-(3-Cyclopenxyloxy-4-methoxyphenyl0-2-(4-pyridyl)ethenyl]benzoic acid;
Ethyl N-{4-[1-(3-Cyclopentyloxy-4-methoxyphenyl)-2-(4-pyridyl) ethenyl]phenyl}carbamate;
N-{4-[1-(3-Cyclopentyloxy-4-methoxyphenyl)-2(4-pyridyl)ethenyl]phenyl}N'-ethylurea;
N-{4-[1-(3-Cyclopentyloxy-4-methoxyphenyl)]-2-(4-pyridyl)ethenyl}phenylacetamide;
3-[2-(3-Cyclopentyloxy-4-methoxyphenyl)-2-phenylethenyl]pyridine;
4-[2-2(3-Cyclopentyloxy-4-methoxyphenyl)-2-phenylethenyl]pyrimidine;
4-[2-(3-Cyclopentyloxy-4-methoxyphenyl)-2-(4-hydroxymethylphenyl)ethenyl]pyridine;
4-[1-(3-Cyclopentyloxy-4-methoxyphenyl)-2-(4-pyridyl)ethenyl]benzamide;
Ethyl-4-[1-(3-Cyclopentyloxy-4-methoxyphenyl)-2-(4-phenylethenyl]benzoate;
N-{4-[1-(3-Cyclopentyloxy-4-methoxyphenyl)-2-(4-pyridyl)ethenyl]phenyl}methanesulphonamide; or
each enantiomer thereof; and the salts, solvates, hydrates and N-oxides thereof.

Compounds according to the invention are selective and potent inhibitors of PDE IV. The ability of the compounds to act in this way may be simply determined by the tests described in the Examples hereinafter.

The compounds according to the invention are thus of particular use in the prophylaxis and treatment of human diseases where an unwanted inflammatory response or muscular spasm is present and where the elevation of cAMP levels may be expected to prevent or alleviate the inflammation and relax muscles.

Particular uses to which the compounds of the invention may be put include the prophylaxis and treatment of asthma, especially inflamed lung associated with asthma, or in the treatment of inflammatory airway disease, chronic bronchitis, eosinophilic granuloma, psoriasis and other benign and malignant proliferative skin diseases, endotoxic shock, septic shock, ulcerative colitis, Crohn's disease, reperfusion injury of the myocardium and brain, chronic glomerulonephritis, atopic dermatitis, urticaria, allergic rhinitis, adult respiratory distress syndrome, diabetes insipidus, allergic conjunctivitis and vernal conjunctivitis.

Compounds according to the invention may also elevate cAMP in lymphocytes and thereby suppress unwanted lymphocyte activation in immune-based diseases such as rheumatoid arthritis, transplant rejection and graft versus host disease.

For the prophylaxis or treatment of disease the compounds according to the invention may be administered as pharmaceutical compositions, and according to a further aspect of the invention we provide a pharmaceutical composition which comprises a compound of formula (1) together with one or more pharmaceutically acceptable carriers, excipients or diluents.

Pharmaceutical compositions according to the invention may take a form suitable for oral, buccal, parenteral or nasal administration, or a form suitable for administration by inhalation or insufflation.

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles and preservatives. The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds of formula (1) may be formulated for parenteral administration by injection e.g. by bolus injection or continuous infusion. Formulations for injection may be presented in unit dosage form. The compositions for injection may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

In addition to the formulations described above, the compounds of formula (1) may also be formulated as a depot preparation. Such long acting formulations may be administered by implantation or by intramuscular injection.

For nasal administration or administration by inhalation, the compounds for use according to the present invention are conveniently delivered in the form of an aerosol spray presentation for pressurised packs or a nebuliser, with the use of suitable propellant, e.g. dichlorodifluoromethane, trichlorofluoromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispense device may be accompanied by instructions for administration.

The quantity of a compound of the invention required for the prophylaxis or treatment of a particular inflammatory condition will vary depending on the compound chosen, and the condition of the patient to be treated. In general, however, daily dosages may range from around 100 ng/kg to 100 mg/kg, e.g. around 0.01 mg/kg to 40 mg/kg body weight for oral or buccal administration, from around 10 ng/kg to 50 mg/kg body weight for parenteral administration, and around 0.05 mg to around 1000 mg for nasal administration or administration by inhalation or insufflation.

The compounds according to the invention may be prepared by the following processes. The symbols Y, $R^2$, $R^3$, $R^4$, $R^5$, and $X^1$, when used in the formulae below are to be understood to represent those groups described above in relation to formula (1) unless otherwise indicated. In the reactions described below it may be necessary to protect reactive functional groups, for example hydroxy, amino or thiol groups, where these are desired in the final product, to avoid their unwanted participation in the reactions. Conventional protecting groups may be used in accordance with standard practice [see, for example, Green, T. W. in "Protective Groups in Organic Synthesis" John Wiley and Sons, 1981.] It may be that deprotection will form the last step in the synthesis of compounds of formula (1). Thus, for example, compounds of formula (1), wherein $R^3$ and/or $R^4$ contains a carboxylic group may be prepared by deprotecting the corresponding compound wherein $R^3$ and/or $R^4$ contains a protected carboxyl group, such as an oxazolinyl e.g. 4,4-dimethyl-2-oxazolinyl, in the presence of a base, e.g. sodium hydroxide, in an acid solvent, e.g. aqueous hydrochloric acid, at an elevated temperature, e.g. the reflux temperature.

Thus according to a further aspect of the invention, a compound of formula (1) may be prepared by dehydration of an alcohol of formula (3):

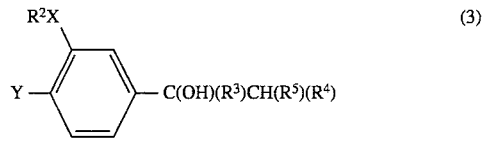

(3)

using an acid or base-catalysed elimination.

Suitable acids include for example phosphoric or sulphonic acids, e.g. 4-toluenesulphonic acid. The reaction may be performed in an inert organic solvent, for example a hydrocarbon such as toluene, at an elevated temperature, for example the reflux temperature. Base catalysed elimination may be performed using for example trifluoroacetic anhydride in the presence of an organic base such as triethylamine at a low temperature e.g. from around 0° C. to ambient temperature, in a solvent such as dichloromethane or tetrahydroduran.

In certain instances, the reaction conditions used may also cleave the group $R^2$ in the starting material of formula (4) to yield a compound of formula (1) where $R^2$ is a hydrogen atom. Such compounds may be converted to the required compound of formula (3) by a further process according to the invention using a halide $R^2$Hal (where Hal is a halogen atom such as a bromine or chlorine atom) where necessary in the presence of a base such as caesium or potassium carbonate or an alkoxide such as potassium t-butoxide, in a dipolar aprotic solvent such as an amide, e.g. a substituted amide such as dimethylformamide at ambient temperature or above e.g. around 40° C. to 50° C.

Intermediates of formula (3) may be prepared by reaction of a ketone of formula (4):

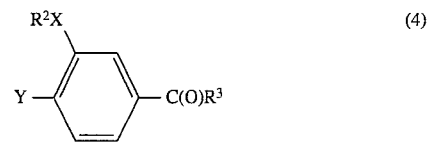

(4)

with an organometallic reagent $R^4R^5CHZ$ where Z is a metal atom.

Metal atoms represented by Z include, for example, a lithium atom.

The reaction may be performed in a solvent such as an ether, e.g. a cyclic ether such as tetrahydrofuran, at a low temperature, e.g. around −70° C. to ambient temperature. This reaction is particularly suitable for the preparation of compounds of formula (1) wherein $R^4$ is an electron deficient group such as a 2- or 4-pyridyl group.

Reagents $R^4R^5CHZ$ are either known compounds or may be prepared, preferably in situ during the above process, by reaction of a compound $AlkCH_2Z$ [where Alk is an alkyl group such as a n-propyl group] with a compound $R^4R^5CH_2$ where necessary in the presence of a base such as an amine e.g. diisopropylamine using the above-mentioned conditions.

Ketones of formula (4) may be prepared by oxidation of a corresponding alcohol of formula (5):

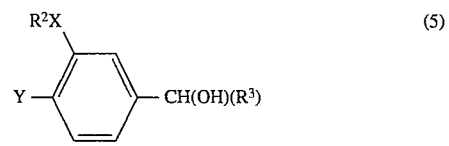

(5)

using an oxidising agent such as manganese dioxide in a solvent such as dichloromethane at ambient temperature.

Alternatively, ketones of formula (4) may be prepared by reaction of a halide of formula (6):

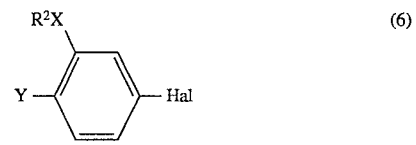

(6)

[where Hal is a halogen atom such as a bromine or chlorine atom] by halogen-metal exchange with a base such as n-butyllithium, followed by reaction with a nitrile $R^3CN$, an acid chloride $R^3COCl$ or an ester $R^3CO_2Alk$ (where Alk is an alkyl group, e.g. a methyl group) in a solvent such as tetrahydrofuran, at a low temperature, e.g. around −70° C., and subsequent treatment with an acid such as hydrochloric acid at e.g. −20° C. to ambient temperature.

Alcohols of formula (5) may be prepared by reaction of an aldehyde of formula (7):

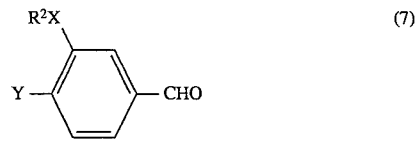

(7)

with organometallic compound, such as an organolithium compound $R^3Li$, or a Grignard reagent $R^3MgBr$, in a solvent, such as tetrahydrofuran, at a low temperature, e.g. around −55° C. to 0° C.

Aldehydes of formula (7) may be prepared by alkylation of a corresponding compound of formula (8):

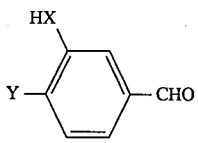 (8)

using a compound $R^2$Hal [where Hal is as previously defined] using the reagents and conditions described herein above for the alkylation of intermediates of formula 4.

Intermediates of formula (8) are either known compounds or may be prepared from known starting materials by methods analogous to those used for the preparation of the known compounds.

Halides of formula (6) may be prepared by alkylation of a compound of formula (9):

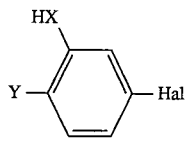 (9)

using the reagents and conditions discussed above in relation to the alkylation of aldehydes of formula (8).

Halides of formula (9) where X is —O— may be prepared by oxidation of an aldehyde of formula (10):

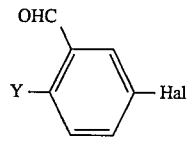 (10)

using an oxidising agent such as 3-chloroperoxybenzoic acid in a halogenated hydrocarbon such as chloroform at a temperature from around 0° C. to room temperature.

Aldehydes of formula (8) and halides of formula (10) where X is —S— or —N($R^6$)— are either known compounds or may be prepared from known starting materials by methods analogous to those used for the preparation of the known compounds.

In yet another aspect of the invention, compounds of formula (1) may be obtained by coupling a compound of formula (11)

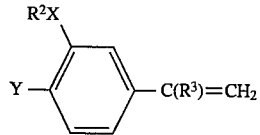 (11)

in a Heck reaction with an organopalladium compound derived from a compound $R^4$Hal [where Hal is a halogen atom, such as a bromine atom] and a palladium salt, such as palladium acetate, in the presence of a phosphine such as tri-o-tolylphosphine and a base such as triethylamine at an elevated temperature and pressure.

Intermediate alkenes of formula (11) may be obtained by reaction of a corresponding ketone of formula (4) (described herein above) using a Wittig reaction employing a phosphonium salt such as methyltriphenylphosphonium bromide in the presence of a base such as n-butyllithium and in inert solvent such as tetrhydrofuran at, for example, 0° C. to ambient temperature.

In a further process according to the invention a compound of formula (1) may be prepared by dehydrogenation of a compound of formula (12):

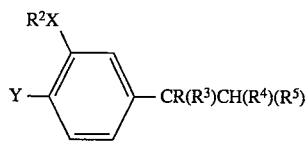 (12)

where R is ahydrogen atom,
using a dehydrogenating agent.

Suitable dehydrogenation reagents include for example quinones such as 2,3-dichloro-5,6-dicyano-1,4-benzoquinone, in a solvent, e.g. dioxane, at an elevated temperature, e.g. the reflux temperature.

Compounds of formula (12) may be prepared by cyclisation of a compound of formula (13)

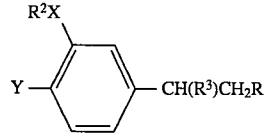 (13)

where R is a carboxylic acid [—$CO_2H$] group or a reactive derivative thereof; or a nitrile [—CN] or an imine salt with a bifunctional reagent $W^1R^{4a}W^2$ and, where necessary, a compound $R^{4b}W^3$ [where $W^1$, $W^2$ and $W^3$, which may be the same or different, is each a reactive functional group or a protected derivative thereof; and $R^{4a}$ and $R^{4b}$ are components of the heteroaryl group $R^4$ such that when added together with $W^1$, $W^2$ and $W^3$ to the group R in compounds of formula (15) the resulting group —$RW^1R^{4a}W^2$ or —$RW^1R^{4a}W^2R^{4b}W^3$ constitutes the heteroaryl group $R^4$].

Reactive derivatives of carboxylic acids for use in this reaction include acid halides, (e.g. acid chlorides), amides, including thioamides, or esters, including thioesters. Imine salts include for example salts of formula [e.g. —C(OAlk)=$NH_2^+A^-$, where Alk is a $C_{1-4}$alkyl group and $A^-$ is a counterion e.g. a chloride ion].

in this general reaction the reactive functional groups represented by $W^1$, $W^2$ or $W^3$ may be any suitable carbon, nitrogen, sulphur or oxygen nucleophiles. Particular examples include simple nucleophiles such as carbanions [e.g. generated by the coupling of an alkyl group with an organometallic compound], amino, thiol and hydroxyl groups.

In general, the cyclisation reaction will initially be performed in a solvent, for example an inert solvent such as a halocarbon, e.g. dichloromethane, an ether, e.g. a cyclic ether such as tetrahydrofuran, or a hydrocarbon, e.g. an aromatic hydrocarbon such as toluene, from a low temperature, e.g. around −70° C., to around the reflux temperature, where necessary in the presence of a base or a thiation reagent, e.g. Lawesson's reagent, followed if necessary by heating, to an elevated temperature, e.g. the reflux temperature.

Thus, in one particular example, compounds of formula (12) wherein $R^4$ is a benzothiazolyl, benzoxazolyl or benzimidazolyl group may be prepared by reaction of a compound of formula (13) where R is an acid halide, e.g. acid chloride, with a reagent $W^1R^{4a}W^2$ which is 2-aminothiophenol, 2-hydroxyphenol, or 1,2-diaminobenzene respectively in the presence of a base e.g. an organic amine such as pyridine, in a solvent e.g. a halocarbon such as dichloromethane, from around −70° C. to the reflux temperature.

In another example of the general cyclisation process, a compound of formula (13) where R is an acid halide as described above may be reacted with a compound $W^1R^{4a}W^2$ which is a monoalkylmalonate, e.g. ethyl hydrogen malonate, followed by reaction with a compound $R^{4b}W^3$ which is hydrazine to give a compound of formula (1) wherein $R^4$ is a 5-hydroxypyrazolyl group.

In another variation of the cyclisation process, the halide of formula (13) may be reacted with a compound $W^1R^{4a}W^2$ which is $BrMg(CH_2)_3[—O(CH_2)_2O—]$ followed by reaction in an acid solution with a compound $R^{4b}W^3$ which is methylamine to yield a compound of formula (1) wherein $R^4$ is a N-methyl pyrrole group.

In a further example of the cyclisation process, the halide of formula (13) may be reacted with a compound $W^1R^{4a}W^2$ which is $H_2NNHCSNH_2$ in an aromatic hydrocarbon such as toluene, at an elevated temperature, e.g. around 150° C., followed by treatment with a base, e.g. an inorganic base such as sodium bicarbonate to give a compound of formula (12) wherein $R^4$ is a 1,2,4-triazolyl-5-thiolate group.

Intermediate compounds of formula (13) are particularly useful and form a further aspect of the invention. Active derivatives of the acids of formula (13) and other compounds of formula (13) where R is a nitrile or an imine salt may be prepared from the corresponding acids [where R is —$CO_2H$] using conventional procedures for converting carboxylic acids to such compounds, for example as described in the Examples hereinafter.

Acids of formula (13) [where R is —$CO_2H$] may be prepared by hydrolysing a diester of formula (14)

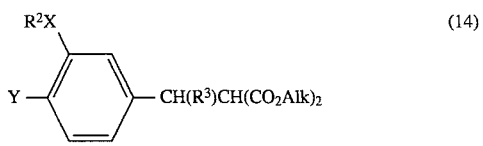

(14)

where Alk is a $C_{1-4}$alkyl group, e.g. an ethyl group, with a base, e.g. sodium hydroxide, in a solvent, e.g. dioxane, at an elevated temperature, e.g. the reflux temperature, followed by acidification at an elevated temperature.

Diesters of formula (14) may be prepared by reacting a diester of formula (15)

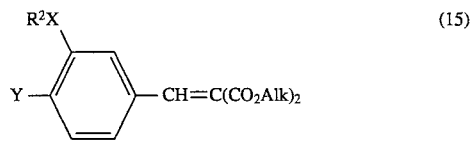

(15)

with an organometallic reagent, such as a Grignard reagent using the conditions described above for the preparation of alcohols of formula (12) (where R is a hydroxy group).

In another process according to the invention, a compound of formula (12) may be prepared by alkylation of a compound of formula (16):

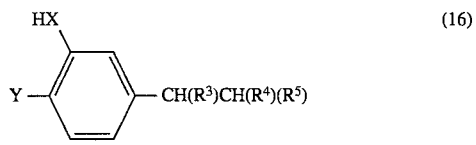

(16)

using a reagent $R^2L$, where L is a leaving group.

Leaving groups represented by L include halogen atoms such as iodine or chlorine or bromine atoms or sulphonyloxy groups such as arylsulphonyloxy groups, e.g. p-toluenesulphonyloxy.

The alkylation reaction may be carried out in the presence of a base, e.g. an inorganic base such as a carbonate, e.g. caesium or potassium carbonate, an alkoxide, e.g. potassium-t-butoxide, or a hydride, e.g. sodium hydride, in a dipolar aprotic solvent such as an amide, e.g. a substituted amide such as dimethylformamide or an ether, e.g. a cyclic ether such as tetrahydrofuran, at ambient temperature or above e.g. around 40° C. to 50° C.

Intermediates of formula (16) may be obtained from the corresponding protected compound of formula (17):

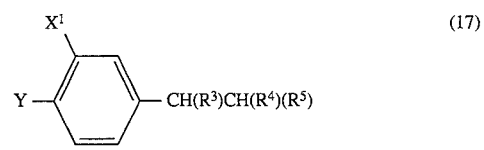

(17)

wherein $X^1$ is a protected hydroxy, thio or amino group using conventional procedures [see Green, T. W. ibid]. Thus, for example, where X is a t-butyldimethylsilyloxy group, the required hydroxyl group may be obtained by treatment of the protected intermediate with tetrabutylammonium fluoride. The protected intermediate of formula (16) may be prepared in an analogous manner to the compounds of formula (1) using the reactions described herein and appropriately protected intermediates.

Compounds of formula (15) may be prepared by condensing an aldehyde of formula (7) with a malonate, e.g. diethylmalonate, if necessary in the presence of catalysts, e.g. piperidine and acetic acid, in an inert solvent, e.g. toluene, at elevated temperature, e.g. the reflux temperature.

Compounds of formula (1) may also be prepared by interconversion of other compounds of formula (1). Thus, for example, a group represented by $R^3$ or $R^4$ in compounds of formula (1) may be substituted in the aryl or heteroaryl portions by any of the groups $R^7$ by an appropriate substitution reaction using the corresponding unsubstituted compound of formula (1) and a $R^7$ containing nucleophile or electrophile.

In another example of an interconversion process a compound of formula (1) wherein the aryl or heteroaryl group in $R^3$ or $R^4$ contains a —$CH_2NH_2$ substituent may be prepared by reduction of a corresponding compound wherein $R^5$ contains a nitrile group, using for example a complex metal hydride such as lithium aluminium hydride in a solvent such as an ether e.g. diethylether.

In a further example, a compound of formula (1) wherein the aryl or heteroaryl group in $R^3$ and/or $R^4$ contains an alkanoylamino or alkanoylaminoalkyl substituent may be prepared by acylation of a corresponding compound wherein $R^3$ and/or $R^4$ contains a —$NH_2$ or alkylamino group by reaction with an acyl halide in the presence of a base, such as a tertiary amine e.g. triethylamine in a solvent such as dichloromethane.

In yet another example of an interconversion process, compounds of formula (1) wherein $R^3$ and/or $R^4$ is substituted by an ester [$CO_2Alk^2$], e.g. an ethanoate, may be prepared by esterification of a corresponding compound wherein $R^3$ and/or $R^4$ contains a carboxylic acid, using an acid halide, such as an acid chloride, e.g. acetyl chloride, in an alcohol, such as ethanol, at an elevated temperature, such as the reflux temperature.

Compounds of formula (1) wherein $R^3$ and/or $R^4$ is substituted by a carboxylic acid may be prepared from the corresponding compound wherein $R^3$ and/or $R^4$ contains a formyl group, by oxidation with an oxidising agent, e.g. potassium permanganate, in a solvent, such as an alcohol, e.g. tert-butanol, at ambient temperature.

In a further interconversion reaction, compounds of formula (1) wherein $R^3$ and/or $R^4$ is substituted by an aminoalkyl group, such as dimethylaminomethyl, may be prepared by reductive amination of a corresponding compound wherein $R^3$ and/or $R^4$ contains a formyl group, using an amine, e.g. dimethylamine, in the presence of a reducing agent, e.g. sodium cyanborohydride, if necessary in the presence of a catalyst, e.g. ethanolic HCl, in a solvent, such as an alcohol, e.g. methanol, at ambient temperature.

In another example of an interconversion reaction a compound of formula (1) wherein $R^3$ and/or $R^4$ is substituted by a formyl group, may be reduced to the corresponding alcohol, e.g. where $R^3$ and/or $R^4$ contains a hydroxymethyl group, using a reducing agent, e.g. sodium borohydride, in a solvent, such as an alcohol, e.g. ethanol, at a temperature from around 20° C. to ambient temperature. The resulting alcohol may then be converted to the corresponding alkoxy derivative, e.g. methoxymethyl, by reaction with an alkyl halide or alkyl sulphonate using the methods and reagents described above for the alkylation of intermediates of formula (18).

In a further example of an interconversion process compounds of formula (1) wherein $R^3$ and/or $R^4$ contains a carboxamido (—$CONHR^{11}$) or an aminocarbonyl (—NHCOR$^{11}$) group may be prepared by reaction of the corresponding compound wherein $R^3$ and/or $R^4$ contains a —$CO_2H$ or a —$NH_2$ group respectively by reaction with a carbamate, such as isobutyl chloroformate or ethyl chloroformate, in the presence of a base, such as an amine, e.g. triethylamine or N-methylmorpholine, in a solvent, such as dichloromethane, or a mixture of solvents, e.g. tetrahydrofuran and dimethylformamide, at a temperature from around −20° C. to room temperature.

N-oxides of compounds of formula (1) may be prepared by oxidation of the corresponding nitrogen base using an oxidising agent such as hydrogen peroxide in the presence of an acid such as acetic acid, at an elevated temperature, for example around 70° C. to 80° C., or alternatively by reaction with a peracid such as peracetic acid in a solvent, e.g. dichloromethane, at ambient temperature.

Salts of compounds of formula (1) may be prepared by reaction of a compound of formula (1) with an appropriate acid or base in a suitable solvent e.g. an organic solvent such as an ether using conventional procedures.

The following examples illustrate the invention. The following abbreviations are used: DMF—dimethylformamide; THF—tetrahydrofuran; DME—dimethoxyethane; EtOAc—ethyl acetate; $Et_2O$—diethylether; $Et_3N$—triethylamine; $CH_2Cl_2$—dichloromethane; BuLi—butyllithium; LDA—lithium diisopropylamide; EtOH—ethanol; RT—room temperature.

INTERMEDIATE 1

3-Cyclopentyloxy-4-methoxybenzaldehyde $Cs_2CO_3$ (214 g, 0.66 mol) was added to a mixture of 3-hydroxy-4-methoxybenzaldehyde (100 g, 0.66 mol) and cyclopentyl bromide (98 g, 0.66 mol) in anhydrous DMF (500 ml). The reaction mixture was stirred at RT for 16 h then treated with a further portion of cyclopentyl bromide (98 g, 0.66 mol) and $Cs_2CO_3$ (214 g, 0.66 mol). After a further 6 h at RT, the mixture was filtered and concentrated in vacuo. The residue was dissolved in $CH_2Cl_2$ (300 ml) and washed with NaOH solution (10%; 2×150 ml). The organic layer was dried ($MgSO_4$), concentrated in vacuo, and distilled (150° C., $10^{-2}$ mbar) to afford the title compound (130 g) as a viscous colourless oil. $\delta_H$ (CDCl$_3$) 1.5–2.0 (8H, br m, (C$\underline{H}_2$)$_4$), 3.87 (3H, s, O$\underline{Me}$), 4.80 (1H, br m, OC$\underline{H}$CH$_2$), 6.90 (1H, d, J 8.7 Hz, Ar$\underline{H}$ ortho to OMe), 7.30–7.45 (2H, m, 2×Ar$\underline{H}$ meta to OMe), and 9.77 (1H, s, ArC$\underline{H}$O).

INTERMEDIATE 2

(3-Cyclopentyloxy-4-methoxyphenyl)phenylketone

Phenyllithium (1.5M in ether-cyclohexane, 33.5 ml, 50 mmol) was added dropwise to a solution of Intermediate 1 (10.0 g, 45.4 mmol) in THF (50 ml) at about −55° C. The reaction mixture was allowed to warm to RT overnight then diluted with water (100 ml) and extracted with $Et_2O$ (3×50 ml). The organic extract was washed with aqueous HCl (1%, 70 ml), brine (100 ml), then dried (MgSO$_4$), and concentrated in vacuo to afford 1-(3-cyclopentyloxy-4-methoxyphenyl)-1-phenylmethanol (13.4 g) as a white solid. m.p. 82.5°–83° C.; $\delta_H$ (CDCl$_3$) 1.5–2.0 (8H, br, m, (C$\underline{H}_2$)$_4$), 2.30 (1H, br, s, O$\underline{H}$), 3.77 (3H, s, O$\underline{Me}$), 4.68 (1H, br, m, OC$\underline{H}$CH$_2$), 5.77 (1H, s, C$\underline{H}$OH), 6.75–6.85 (3H, m, Ar$\underline{H}$ ortho to OMe+2×Ar$\underline{H}$ meta to OMe), and 7.15–7.4 (5H, m, C$_6$H$_5$); m/z 298 (M$^+$ 20%), 230 (50), 151 (30), 125 (100), 124 (33), 105 (38), and 92 (22).

The alcohol (prepared above) (13.4 g, 44.8 mmol) was dissolved in $CH_2Cl_2$ (150 ml) and treated with $MnO_2$ (22 g). The reaction mixture was vigorously stirred at RT for 18 h then treated with a further portion of $MnO_2$ (20 g). More $MnO_2$ (20 g) was added after 10 h and the mixture stirred for 18 h then filtered through Celite® and concentrated in vacuo. The residue was recrystallised from EtOH to afford the title compound (11.27 g; two crops) as a white crystalline solid m.p. 59°–75° C.; $\delta_H$ (CDCl$_3$) 1.5–2.1 (8H, br, m, (C$\underline{H}_2$)$_4$), 3.88 (3H, s, OMe), 4.80 (1H, br m, OC$\underline{H}$CH$_2$), 6.83 (1H, d, J 8.5 Hz, Ar$\underline{H}$ ortho to OMe), and 7.25–7.8 (7H, m, 2×Ar$\underline{H}$ meta to OMe+C$_6\underline{H}_5$); m/z 296 (M$^+$ 11%), 229 (17), 228 (95), 152 (12), 151 (100), 105 (30), 77 (21), and 41 (10).

INTERMEDIATE 3

5-Bromo-2-methoxyphenol

A solution of 5-bromo-2-methoxybenzaldehyde (100 g, 0.46 mol) in CHCl$_3$ (150 ml) was cooled with an ice bath and 3-chloroperoxybenzoic acid (50–60% purity) (146 g, 0.51 mol) in CHCl$_3$ (1000 ml) added. The reaction mixture was allowed to warm slowly to room temperature and stirred for 72 h. The white solid was filtered off and the filtrate concentrated in vacuo. The residue was dissolved in Et$_2$O (200 ml) and washed with 1M sodium sulphite solution (2×200 ml) then NaHCO$_3$ [half saturated] (3×200 ml). The ether layer was washed with 10% aqueous NaOH (3×100 ml) and the combined basic extract was acidified with concentrated hydrochloric acid and extracted with Et$_2$O (3×100 ml). The combined organic extract was dried (MgSO$_4$) and florisil (10 g) filtered and the solvent removed under reduced pressure to give the title compound (90 g) as a pale brown solid.

INTERMEDIATE 4

4-Bromo-2-cyclopentyloxyanisole

Intermediate 3 (90 g)was dissolved in DMF (300 ml), and treated with Cs$_2$CO$_3$ (158 g, 490 mmol), and cyclopentyl bromide (73 g, 52.5 ml, 490 mmol). After stirring overnight, further CS$_2$CO$_3$ (35 g, 107 mmol) and cyclopentylbromide (12 ml, 16.7 g, 112 mmol) were added and stirring continued for 2 h. Further portions of cyclopentylbromide (10 ml) and CS$_2$CO$_3$ were then added (14 g). After stirring for 1 h, the DMF was evaporated in vacuo and the residue diluted with water (200 ml) and extracted with Et$_2$O (3×100 ml). The combined organic extract was washed with NaOH solution (5%, 2>100 ml), water (100 ml), then dried (MgSO$_4$) and the solvent evaporated in vacuo to give a red oil which was distilled (140° C., 0.3 mbar) to afford the title compound (101 g) as a colourless oil (Found: C, 53.11; H, 5.53. C$_{12}$H$_{15}$BrO$_2$ requires C, 53.15; H, 5.58%).

INTERMEDIATE 5

(3-Cyclopentyloxy-4-methoxyphenyl)(4-pyridyl)ketone n-BuLi (1.45M in hexanes; 19.6 ml, 28.4 mmol) was added dropwise at −70° C. to a solution of Intermediate 4 (7.0 g, 25.8 mmol) in THF (50 ml). After stirring for 0.25 h, a solution of 4-cyanopyridine (3.08 g, 29.7 mmol) in THF (15 ml) was added and maintained at −70° C. for 0.75 h. The reaction mixture was then allowed to warm to −10° C. and quenched with aqueous HCl (10%; 60 ml). The mixture was stirred for 0.5 h, basified with aqueous NaOH (10%, 70 ml), and extracted with $Et_2O$ (3×70 ml). The extract was washed with brine (100 ml), dried ($MgSO_4$), and concentrated in vacuo, The residue was subjected to chromatography ($SiO_2$; EtOAc/hexane, 4:1) to afford the title compound (6.34 g) as a white powder. $\delta_H$ ($CDCl_3$) 1.5–1.9 (8H, br m, $(CH_2)_4$), 3.90 (3H, s, OMe), 4.82 (1H, br m, OCHCH$_2$), 6.84 (1H, d, J 8.4 Hz, ArH ortho to OMe) 7.29 (1H, dd, J 8.4, 2.0 Hz, Ar H para to cyclopentyloxy), 7.4–7.55 (3H, m, ArH ortho to cyclopentyloxy+pyridine H$_3$, H$_5$), and 8.73 (2H, dd, J 4.4 Hz, 1.5 Hz, pyridine H$_2$, H$_6$).

INTERMEDIATE 6

(E) and (Z) isomers of 4-[1-(3-Hydroxy-4-methoxyphenyl)-2-(4-pyridyl) ethenyl]pyridine Intermediate 8 (0.72 g, 1.85 mmol) in toluene (120 ml) containing 4-toluenesulphonic acid (0.88 g, 4.6 mmol) was heated to reflux in a Dean-Stark apparatus for 18 h. The cooled reaction mixture was treated with aqueous NaOH (10%) then taken to pH 7 with concentrated hydrochloric acid. The mixture was extracted with $CH_2Cl_2$ (3×40 ml), the extract washed with saturated $NaHCO_3$ (100 ml), and $Na_2CO_3$ (10%; 2×60 ml), then dried ($MgSO_4$), and concentrated in vacuo to afford the title compound (0.4 g) as a yellow foam; $\delta_H$ ($CDCl_3$) (major isomer) 3.88 (3H, s, OMe), 6.6–6.9 (6H, m, ArH ortho to OMe+2×ArH meta to OMe+C=CH+pyridine H$_3$, H$_5$), 7.08 (2H, dd, J 4.6, 1.6 Hz, pyridine H$_3$, H$_5$), 8.30 (2H, dd, J 4.5, 1.6 Hz, pyridine H$_2$, H$_6$), and 8.51 (2H, dd, J 4.4, 1.6 Hz, pyridine H$_2$, H$_6$), [the minor isomer displays a signal at δ 3.90 (3H, s, OMe)].

INTERMEDIATE 7 a)    (±)-4-[2-(3-Cyclopentyloxy-4-methoxyphenyl)-2-hydroxy-2-phenylethyl]pyridine n-Buli (1.4M in hexanes; 2.7 ml, 3.7 mmol) was added dropwise at −70° C. to a solution of 4-methylpyridine (0.35 g, 3.72 mmol) in THF (20 ml). After 0.5 h, a solution of Intermediate 2 (1.00 g, 3.38 mmol) in THF (4 ml) was added over 5 min at −70° C., the mixture stirred for 1 h at this temperature then allowed to warm to RT over 2 h. The reaction mixture was partitioned between $Et_2O$ (50 ml) and water (50 ml) and the organic layer was separated. The aqueous layer was further extracted with $Et_2O$ (2×40 ml) and the combined organic extract was dried ($MgSO_4$) and concentrated in vacuo. The residue was subjected to chromatography ($SiO_2$; EtOAc-hexane) to afford, first, Intermediate 2 (300 mg) then the title compound (738 mg) as a white solid. m.p. 148°–149° C. (toluene-hexane)(Found: C, 77.32; H, 7.04; N, 3.50. $C_{25}H_{27}O_3$ requires C, 77.09; H, 6.99; N, 3.60%); $\delta_H$ ($CDCl_3$) 1.4–1.9 (8H, br, m, $(CH_2)_4$), 2.3 (1H, v.br.s, OH exchanges with $D_2O$), 3.51 (2H, s, $CH_2$ pyridine), 3.78 (3H, s, OMe), 4.60 (1H, br, m, OCHCH$_2$), 6.65–6.9 (5H, m) and 7.15–7.4 (5H, m) (ArH ortho to OMe+2×Ar H meta to OMe+$C_6H_5$+pyridine H$_3$, H$_5$), and 8.22 (2H, dm, J 4.5 Hz, pyridine H$_2$, H$_6$): m/z 389 (M$^+$ 3%), 298 (15), 297 (69), 229 (27), 228 (37), 151 (43), 105 (100), 93 (52), 77 (24), and 41 (14).

The following compounds were prepared in a manner similar to Intermediate 7a.

b)    (±)-2-[2-(3-Cyclopentyloxy-4-methoxyphenyl)-2-hydroxy-2-phenylethyl]pyrazine From 2-methylpyrazine (1.0 ml, 110 mmol) and Intermediate 2 (3.24 g, 11.0 mmol). Trituration with $Et_2O$ gave the title compound (0.885 g) as a white solid. $\delta_H$ ($CDCl_3$) 1.45–1.9 (8H, br, m, $(CH_2)_4$), 3.73 (2H, s, $CH_2$ pyrazine), 3.80 (3H, s, OMe), 4.68 (1H, br, m, OCH), 6.22 (1H, br s, OH), 6.73 (1H, d, J 8.4 Hz, ArH Ortho to OMe), 6.89 (1H, dd, J 8.4, 2.0 Hz, ArH para to cyclopentyloxy), 7.0 (1H, d, J 2.0 Hz, ArH ortho to cyclopentyloxy), 7.1–7.5 (5H, m, $C_6H_5$), and 8.37 (3H, s, pyrazine H$_3$, H$_5$ H$_6$).

c)    (±)-4-[2-(3-Cyclopentyloxy-4-methoxyphenyl)-2-hydroxyphenylethyl]-3,5-dichloropyridine From Intermediate 11 (2.0 g, 12.3 mmol) and Intermediate 2 (3.65 g, 12.3 mmol). Purification by column chromatography ($SiO_2$; 0–2% MeOH/$CH_2Cl_2$) afforded the title compound (1.74 g) as a white solid. m.p. 129°–130° C. $\delta_H$ ($CDCl_3$) 1.5–1.9 (8H, br, m, $(CH_2)_4$), 2.65 (1H, br s, OH), 3.85 (3H, s, OMe), 3.92 (1H, d, J 14 Hz, CH$_A$H$_B$ pyridine), 3.98 (1H, d, J 14 Hz, CH$_A$H$_B$ pyridine), 4.57 (1H, br, m, OCH), 6.7–6.9 (3H, m, ArH Ortho+2×ArH meta to OMe), 7.2–7.4 (5H, m, $C_6H_5$), and 8.36 (2H, s, pyridine H$_2$, H$_6$).

d)    4-[2-(4-Bromophenyl)-2-(3-cyclopentyloxy-4-methoxyphenyl)-2-hydroxyethyl]pyridine From 4-picoline (2.0 ml, 1.90 g, 20.4 mmol) and Intermediate 26 (7.30 g, 19.5 mmol). Purification by column chromatography ($SiO_2$; gradient elution 50–75%, EtOAc/hexane) gave the title compound (7.77 g) as a pale yellow foamy solid. Found: C, 63.82; H, 5.58; N, 2.96. $C_{25}H_{26}BrNO_3$ requires C, 64.11; H, 5.60; N, 2.99%. $\delta_H$ ($CDCl_3$) 1.5–1.9 (8H, br, m, $(CH_2)_4$), 2.7 (1H, br s, OH), 3.46 (1H, d, J 13.1 Hz, CH$_A$H$_B$ pyridine), 3.54 (1H, d, J 13.1 Hz, CH$_A$H$_B$ pyridine), 3.82 (3H, s, OMe), 4.64 (1H, br m, OCH), 6.75–6.9 (5H, m, $C_6H_3$+pyridine H$_3$, H$_5$), 7.21 (2H, ca. d, J 8.7 Hz, ArH of $C_6H_4$), and 8.29 (2H, ca. d, J 6.0 Hz, pyridine H$_2$, H$_6$); $\nu_{max.}$ ($CDCl_3$) 3604, 1605, 1513, and 1256 cm$^{-1}$; m/z (ESI) 470 (M$^+$+2, 20%), 468 (M$^+$, 18), 377 (52), 375 (55), 95 (13), and 94 (100).

e)    (±)-4-{2-(3-Cyclopentyloxy-4-methoxyphenyl)-2-[4-(4,4-dimethyl-2-oxazolinyl)phenyl]-2-hydroxyethyl}pyridine From 4-methylpyridine (1.45 g, 1.52 ml, 15.6 mmol) and Intermediate 14 (5.82 g, 14.9 mmol). Trituration with $Et_2O$ gave the title compound (6.61 g) as an off-white solid. $\delta_H$ ($CDCl_3$) 1.37 (6H, s, CMe), 1.55–1.8 (8H, m, $(CH_2)_4$), 2.7 (1H, v. br s, OH) 3.56 (2H, br s, $CH_2$ pyridine), 3.82 (3H, s, OMe), 4.10 (2H, s, oxazoline $CH_2$), 4.63 (1H, m, OCH), 6.75–6.9 (5H, m, ArH), 7.37 (2H, d, J 8.6 Hz, pyridine H$_3$, H$_5$), 7.85 (2H, d, J 7.3 Hz, ArH ortho to oxazoline) and 8.29 (2H, br s, pyridine H$_2$, H$_6$); $\nu_{max.}$ ($CDCl_3$) 3603, 1649, 1512, and 1257 cm$^{-1}$; m/z (ESI) 487 (M$^+$+1, 100%), and 394 (61).

f) 4-[2-(3-Cyclopentyloxy-4-methoxyphenyl)-2-hydroxy-2-(2-thienyl)ethyl]pyridine From 4-picoline (0.94 g, 10.1 mmol)in THF (80 ml) and Intermediate 18 (3.06 g, 10.1 mmol)in THF (20 ml). Chromatography ($SiO_2$; $Et_2O$ to EtOAc/hexane, 4:1) afforded the title compound (3.32 g) as a white foam m.p. 57°–67° C. (Found C, 69.82; H, 6.42; N, 3.41. $C_{23}H_{25}NO_3S$ requires C, 69.85; H, 6.37; N, 3.54%); $\delta_H$ ($CDCl_3$) 1.5–2.0 (8H, m, (C H$_2$)$_4$), 3.0 (1H, br s, OH), 3.50 (1H, d, J 13.2 Hz pyridine C H$_A$H$_B$), 3.58 (1H, d, J 13.2 Hz, pyridine CH$_A$H$_B$), 3.83 (3H, s, OMe), 4.64 (1H, m, OCH), 6.75–6.8 (1H, m, ArH of

19

C$_6$H$_3$), 6.85–7.05 (6H, m, 2×ArH of C$_6$H$_3$+pyridine H$_3$, H$_5$+thiophene H$_3$, H$_4$), 7.25 (1H, dd, J 4.7, 1.7 Hz, thiophene H$_5$), and 8.29 (2H, ca d, J 6.0 Hz, pyridine H$_2$, H$_6$); m/z (ESI) 418 (M$^+$+Na, 10%), 396 (M$^+$+1, 100), 303 (35), 95 (12), and 94 (72).

The alcohol was then dehydrated using the procedure described in Example 7.

INTERMEDIATE 8

(±)-4-[1-(3-Cyclopentyloxy-4-methoxyphenyl)-1-hydroxy-2-(4-pyridyl) ethyl]pyridine n-BuLi (1.45M in hexanes; 5.1 ml, 7.41 mmol) was added dropwise at −70° C. to a solution of 4-methylpyridine (0.69 g, 7.41 mmol) in THF (20 ml). After 0.5 h a solution of Intermediate 5 (2.0 g, 6.73 mmol) in THF (10 ml) was added dropwise over 5 min. The reaction mixture was stirred for 0.5 h at −70° C. then at RT for 0.5 h. Water (50 ml) was added and the mixture extracted with EtOAc (3×60 ml). The extract was washed with brine (80 ml), dried (MgSO$_4$), and concentrated in vacuo. The residue was subjected to chromatography (SiO$_2$; EtOAc to EtOAc/CH$_3$OH, 9:1) to afford the title compound (2.33 g) as a white amorphous solid m.p. 99°–103° C; δ$_H$ (CDCl$_3$) 1.5–2.0 (9H, br, m, (CH$_2$)$_4$+OH), 3.49 (2H, d, J 2.3 Hz, CH$_2$ COH), 4.65 (1H, br m, OCHCH$_2$), 6.7–6.9 (5H, m, ArH ortho to OMe+2×ArH meta to OMe+pyridine H$_3$, H$_5$), 7.20 (2H, dd, J 4.6, 1.6 Hz, pyridine H$_3$, H$_5$), 8.22 (2H, dd, J 4.6, 1.6 Hz, pyridine H$_2$, H$_6$), and 8.40 (2H, dd, J 4.6, 1.6 Hz, pyridine H$_2$, H$_6$); m/z 390 (M$^+$ 3%), 298 (21), 297 (14), 230 (21), 229 (91), 151 (100), 106 (22), 93 (27), 78 (12), and 41 (23).

INTERMEDIATE 9

1-(3-Cyclopentyloxy-4-methoxyphenyl)-1-phenylethene

To a cold suspension (0° C.) of methyl triphenylphosphonium bromide (53.6 g; 0.15 mol) in THF (500 ml) under a nitrogen atmosphere was added n-BuLi (1.6M in hexanes; 94 ml, 0.15 mol) dropwise and the reaction mixture stirred at 0° C, for 1 h. A solution of Intermediate 2 (29.6 g, 0.1 mol) in THF (100 ml) was added dropwise and the stirred reaction mixture allowed to warm to RT over 3 h. The mixture was poured into 10% NH$_4$Cl solution (600 ml) and extracted with CH$_2$Cl$_2$ (2×500 ml). The combined organic layer was dried (MgSO$_4$), filtered and concentrated in vacuo. The residual slurry was triturated with hot hexane (500 ml), the precipitated phosphine oxide filtered off and the filtrate evaporated in vacuo to yield the title compound (28.85 g) as a yellow oil. δ$_H$ (CDCl$_3$) 1.5–2.0 (8H, br m, (CH$_2$)$_4$), 3.85 (3H, s, OMe), 4.71 (1H, br m, OCH), 5.38 (2H, dd, J 10.5, 1.3 Hz, C=CH$_2$), 6.75–6.9 (3H, m, C$_6$H$_3$), and 7.3–7.5 (5H, m, C$_6$H$_5$).

INTERMEDIATE 10 a) (±)-3-[2-(3-Cyclopentyloxy-4-methoxyphenyl)-2-hydroxy-2-phenylethyl]-2-methoxypyrazine n-BuLi (1.6M in hexanes; 6 ml, 12 mmol) was added dropwise at 4° C. to a solution of N,N-diisopropylamine (1.85 ml, 13 mmol) in THF (40 ml). After 0.5 h, 2-methoxy-3-methylpyrazine (1.28 ml, 11 mmol) was added dropwise at −70° C. and the mixture stirred for 2 h at this temperature. A solution of Intermediate 2 (3.26 g, 11 mmol) in THF (20 ml) was added over 10 min at −70° C. and the mixture stirred for a further 1 h and then allowed to warm to RT. The reaction mixture was partitioned between CH$_2$Cl$_2$ (75 ml) and saturated NaHCO$_3$ (100 ml). The organic layer was separated, combined with further CH$_2$Cl$_2$ extracts (2×75 ml), dried (MgSO$_4$) and concentrated in vacuo. The residue was subjected to chromatography (SiO$_2$; CH$_2$Cl$_2$) to afford the title compound (2.94 g) as a white foam. δ$_H$ (CDCl$_3$) 1.5–2.0 (8H, br m, (CH$_2$)$_4$), 3.63 (1H, d, J 14 Hz, CHH pyrazine), 3.77 (1H, d, J 14 Hz, CHH pyrazine), 3.79 (3H, s, OMe ortho to cyclopentyloxy), 3.97 (3H, s, pyrazine OMe), 4.67 (1H, br m, OCH), 6.72 (1H, dd, J 8.4 Hz, ArH ortho to OMe), 6.77 (1H, s, OH), 6.91 (1H, dd, J 8.4 Hz, 2.0 Hz, ArH para to cyclopentyloxy), 7.00 (1H, d, J 2.0 Hz, ArH ortho to cyclopentyloxy), 7.1–7.5 (5H, m, C$_6$H$_5$), and 7.85–7.95 (2H, m, pyrazine H$_5$, H$_6$).

b) (±)-2-[-2-(3-Cyclopentyloxy-4-methoxyphenyl)-2-hydroxy-2-phenylethyl]-4-methylpyridine From 2,4-dimethylpyridine (1.7 ml, 14.5 mmol) and Intermediate 2 (4.30 g, 14.5 mmol). Purification by chromatography (SiO$_2$; CH$_2$Cl$_2$) afforded the title compound (1.23 g) as a colourless oil (Found: C, 77.07; H, 7.10; N, 3.25. C$_{26}$H$_{29}$NO$_3$ requires C, 77.39; H, 7.24; N, 3.47%); δ$_H$ (CDCl$_3$) 1.4–1.9 (8H, br m, (CH$_2$)$_4$), 2.25 (3H, s, pyridine Me), 3.60 (2H, s, CH$_2$ pyridine), 3.77 (3H, s, OMe), 4.68 (1H, br m, OCH), 6.72 (1H, d, J 8.5 Hz, ArH ortho to OMe), 6.8–6.95 (3H, m, ArH para to cyclopentyloxy+pyridine H$_3$, H$_5$), 7.02 (1H, d, J 2.2 Hz, ArH ortho to cyclopentyloxy), 7.1–7.3 (3H, m, meta and para ArH of C$_6$H$_5$), 7.46 (2H, ca d, J 8.5 Hz, ortho ArH of C$_6$H$_5$), and 8.23 (1H, ca d, J 6 Hz, pyridine H$_6$); m/z (ESI) 404 (M$^+$+1, 72%), 387 (13), and 386 (100).

c) (±)-4-[2-(3-Cyclopentyloxy-4-methoxyphenyl)-2-hydroxy-2-phenylethyl]pyrimidine From 4-methylpyrimidine (1.0 ml) and Intermediate 2 (3.98 g). Purification by chromatography (SiO$_2$;CH$_2$Cl$_2$) afforded the title compound (2.56 g) as a white solid; δ$_H$ (CDCl$_3$) 1.5–2.0 (8H, br m, (CH$_2$)$_4$), 3.66 (2H, s, CH$_2$ pyrimidine), 3.77 (3H, s, OMe), 4.65 (1H, br m, OCH), 6.58 (1H, s, OH), 6.72 (1H, d, J 8.4 Hz, ArH ortho to OMe), 6.85 (1H, dd, J 8.4, 2.2 Hz, ArH para to cyclopentyloxy), 6.98 (1H, d, J 2.2 Hz, ArH ortho to cyclopentyloxy), 7.07 (1H, d, J 5.2 Hz, pyrimidine H$_5$), 7.15–7.45 (5H, m, C$_6$H$_5$), 8.53 (1H, d, J 5.2 Hz, pyrimidine H$_6$), and 8.99 (1H, s, pyrimidine H$_2$).

d) (±)-3-[2-(3-Cyclopentyloxy-4-methoxyphenyl)-2-hydroxy-2-phenylethyl]pyridazine From 3-methylpyridazine (1.0 ml) and Intermediate 2 (3.98 g). Purification by chromatography (SiO$_2$; EtOH—CH$_2$Cl$_2$) afforded the title compound (4.02 g) as an off-white solid.

INTERMEDIATE 11

3,5-Dichloro-4-methylpyridine 3,5-Dichldropyridine (2.04 g, 13.5 mmol) in THF (5 ml) was added dropwise to a solution of LDA [prepared from diisopropylamine (1.9 ml, 13.5 mmol) and n-BuLi (1.6M; 8.4 ml, 13.5 mmol)] in THF (25 ml) at −70° C. After stirring at this temperature for 5 min, iodomethane (0.85 ml, 13.5 mmol) was added and the reaction mixture stirred for a further 1.5 h at −70° C. Saturated NaHCO$_3$ (20 ml) and CH$_2$Cl$_2$ (20 ml) were added, the organic phase separated, dried (MgSO$_4$), and concentrated in vacuo. The residue was subjected to chromatography (SiO$_2$; Et$_2$O/hexane, 1:3) to afford the title compound (1.16 g) as a pale yellow solid. δ$_H$ (CDCl$_3$) 2.46 (3H, s, Me), and 8.36 (2H, s, pyridine H$_2$, H$_6$).

INTERMEDIATE 12

(4-Bromophenyl)(3-cyclopentyloxy-4-methoxyphenyl)ketone

A solution of Intermediate 4 (8.00 g, 29.5 mmol) in THF (50 ml) at −70° C. was treated with n-BuLi (19.4 ml, 31.0 mmol, 1.6M solution in hexanes). The slightly yellow solution was stirred at −70° C. for 0.5 h then a solution of 4-bromobenzaldehyde (5.46 g, 29.5 mmol) in THF (50 ml) was added via cannula. The reaction was allowed to warm to RT over 2 h then quenched with water (25 ml) and extracted with Et$_2$O (2×50 ml). The extract was dried (MgSO$_4$) and concentrated in vacuo to give a pale yellow oil which was dissolved in CH$_2$Cl$_2$ (150 ml) and treated with manganese dioxide (19.24 g, 0.22 mol). The mixture was stirred vigorously for 20 h at RT then filtered through Celite® and the residue washed with CH$_2$Cl$_2$ (5×50 ml). The filtrate was concentrated in vacuo to give an off-white solid which was triturated with hexane to give the title compound (7.50 g) as a white solid; δ$_H$ (CDCl$_3$) 1.55–2.05 (8H, m, (CH$_2$)$_4$), 3.92 (3H, s, OMe), 4.83 (1H, m, OCH), 6.89 (1H, d, J 8.4 Hz, ArH ortho to OMe), 7.33 (1H, dd, J 8.4, 2.0 Hz, ArH para to OMe), 7.42 (1H, d, J 2.0 Hz, ArH ortho to cyclopentyloxy), and 7.55–7.7 (4H, m, C$_6$H$_4$); ν$_{max.}$ (CDCl$_3$) 2248, 1652, 1590, and 1270 cm$^{-1}$; m/z (ESI) 399 (M$^+$+2+Na, 100%), 397 (M$^+$+Na, 90), 296 (16), and 236

INTERMEDIATE 13

Ethyl (E)-(3-Cyclopentyloxy-4-methoxyphenyl)-2-(4-pyridyl) propenoate

A mixture of Intermediate 1 (26.62 g, 0.12 mol), ethyl-4-pyridylacetate (19.92 g, 0.12 mol, 1 eq) and ammonium acetate (18.63 g, 0.24 g, 2 eq) in glacial acetic acid (200 ml) was stirred at 120° C. under nitrogen for 20 h. The solution was cooled to RT and the acid removed in vacuo. The orangy/brown residue was taken up in saturated NaHCO$_3$ solution to pH 8.5 and the aqueous layer extracted several times with EtOAc. The combined organic layer was washed (brine), dried (MgSO$_4$) and evaporated to dryness to give a yellow solid. Recrystallisation from toluene/hexane (1st crop) then toluene (2nd crop) followed by column chromatography (hexane-EtOAc/hexane, 7:3) gave the title compound as a white crystalline solid. m.p. 109°–110° C. δ$_H$ (CDCl$_3$) 1.27 (3H, t, J 7.1 Hz, CH$_2$CH$_3$), 1.45–1.8 (8H, br m, cyclopentyl H's), 3.81 (3H, s, OMe), 4.16 (1H, br m, OCH), 4.25 (2H, q, J 7.1 Hz, CH$_2$CH$_3$), 6.43 (1H, d J 2.0 Hz, ArH ortho to cyclopentyloxy), 6.73 (1H, d, J 8.4 Hz, ArH ortho to OMe), 6.80 (1H, dd, J 2.0, 8.4 Hz, ArH para to cyclopentyloxy), 7.22 (2H, dd, J 1.6, 4.5 Hz, pyridine H$_3$, H$_5$), 7.83 (1H, s, HC=C) and 8.64 (2H, dd, J 1.6, 4.5 Hz, pyridine H$_2$, H$_6$).

INTERMEDIATE 14

4-(4,4-dimethyl-2-oxazolinyl)-3'-cyclopentyloxy-4'-methoxyphenyl) ketone

A solution of 2-(4-bromophenyl)-4,4-dimethyloxazoline (A. J. Meyers, D. L. Temple, D. Haidukewych and E. D. Milhelich J. Org. Chem, 39, 2787, 1974) (53.25 g, 0.21 mol) in THF (200 ml) was added dropwise to magnesium turnings (6.0 g, 0.25 g atoms). The reaction was stirred for 2 h at RT, then a solution of Intermediate 1 (46.0 g, 0.21 mol) in THF (200 ml) was added dropwise. The reaction was stirred for 16 h then heated to reflux for 1 h, cooled to RT and quenched with ammonium chloride solution (200 ml). The layers were separated and the aqueous layer extracted with EtOAc (2×250 ml). The organic layer was washed with brine (250 ml), dried (MgSO$_4$), then concentrated in vacuo to give an orange oil. The crude oil was dissolved in CH$_2$Cl$_2$ (350 ml) and treated with manganese dioxide (137 g, 1.58 mol) then stirred vigorously for 72 h. The mixture was filtered through Celite® and the residue washed with CH$_2$Cl$_2$ (300 ml). The filtrate was concentrated in vacuo and the residue triturated with Et$_2$O to give the title compound (59.4 g) as an off white amorphous powder m.p. 159° C. δ$_H$ (CDCl$_3$) 1.41 (6H, s, CMe$_2$), 1.5–2.1 (8H, m, (CH$_2$)$_4$), 3.92 (3H, s, OMe), 4.15 (2H, s, oxazoline CH$_2$), 4.84 (1H, m, OCH), 6.89 (1H, d, J 8.4 Hz, ArH ortho to OMe), 7.35 (1H, dd, J 2.0, 8.4 Hz, ArH para to OMe), 7.43 (1H, d, J 2 Hz, ArH ortho to cyclopentyloxy), 7.78 (2H, d, J 8.5 Hz, ArH), and 8.03 (2H, d, J 8.5 Hz, ArH); ν$_{max}$ (CDCl$_3$) 1648 and 1271 cm$^{-1}$; m/z (ESI) 394 (M$^+$+1, 100 %).

The following Intermediate was prepared in a manner similar to the compound of Example 7a.

INTERMEDIATE 15

(E) and (Z) isomers of 4-{2-(3-Cyclopentyloxy-4-methoxyphenyl)-2-[4-(4,4-dimethyl-2-oxazolinyl)phenyl]ethenyl}pyridine From the alcohol of Intermediate 7e (4.57 g, 9.8 mmol), trifluoroacetic anhydride (2.47 g, 1.66 ml, 11.8 mmol) and triethylamine (0.99 g, 1.36 ml, 11.8 mmol). A portion (100 mg) of the residue was subjected to chromatography (SiO$_2$; EtOAc) to give the title compound (68 mg) as a yellow foam. δ$_H$ (CDCl$_3$) 1.39, 1.41 (6H, s, CMe$_2$), 1.5–1.95 (8H, m, (CH$_2$)$_4$), 3.85, 3.88 (3H, s, OMe), 4.11, 4.14 (2H, s, oxazoline CH$_2$), 4.55, 4.69 (1H, m, OCH), 6.6–6.7 (1H, m, ArH), 6.8–6.85 (3H, m, ArH), 6.91 (1H, d, J 6.2 Hz, pyridine H$_3$, H$_5$), 7.23, 7.38 (2H, d, J 8.2 Hz, ArH), 7.9–8.0 (2H, m, ArH) and 8.3–8.45 (2H, m, pyridine H$_2$, H$_6$); ν$_{max}$ (CDCl$_3$) 1735, 1646, 1597 and 1318 cm$^{-1}$; m/z (ESI) 469 (M$^+$, 100%).

INTERMEDIATE 16

(±)-4-[2-(3-Cyclopentyloxy-4-methoxyphenyl)-2-(2-furyl)-2-hydroxyethyl]pyridine n-Butyllithium (1.6M solution in hexane; 16.9 ml, 27 mmol) was added to a stirred solution of furan (1.84 g, 1.96 ml, 27 mmol) in THF (25 ml) at −70° C. After 1 h at −70° C., a solution of Intermediate 1 (4.0 g, 18 mmol) in THF (10 ml) was added over 10 min. The reaction mixture was stirred at −70° C. for 0.75 h, warmed to RT over 0.75 h, then quenched with water (100 ml) and extracted with Et$_2$O (3×60 ml). The extract was washed with brine (100 ml), dried (MgSO$_4$), and concentrated in vacuo. The residual orange-yellow oil was subjected to chromatography (SiO$_2$; CH$_2$Cl$_2$/hexane, 3:1, then Et$_2$O/hexane, 1:1) to give (3-cyclopentyloxy-4-methoxyphenyl)(2-furyl)methanol (3.2 g, 61%) as a colourless unstable oil; ν$_{max.}$ (neat) 3500 cm$^{-1}$.

The alcohol (3.2 g) was stirred with manganese (IV) oxide (10 g) in CH$_2$Cl$_2$ (100 ml) at RT for 3 h. The mixture was filtered through Celite® and the filtrate concentrated in vacuo. The residual dark oil was subjected to chromatography (SiO$_2$) to give (3-cyclopentyloxy-4-methoxyphenyl)-(2-furyl)ketone (1.9 g); ν$_{max}$ (neat) 1620 cm$^{-1}$.

n-Butyllithium (1.6M solution in hexanes; 4.2 ml, 6.64 mmol) was added to a solution of a 4-methylpyridine (0.62 g, 0.65 ml, 6.64 mmol) in THF (25 ml) at −70° C. After 0.5 h, a solution of the crude ketone (1.9 g, ca. 6.6 mmol) in THF (5 ml) was added, stirred for 1 h at −70° C., then at RT for 0.25 h. The reaction mixture was quenched with water (50 ml) and extracted with EtOAc (3×50 ml). The extract was dried (MgSO$_4$), concentrated in vacuo, and the residual red oil subjected to chromatography (SiO$_2$; EtOAc/hexane, 3:2) to afford the title compound (1.23 g, 49%) as a pale yellow oil; δ$_H$ (CDCl$_3$) 1.5–1.9 (8H, br m, (CH$_2$)$_4$), 2.84 (1H, br s, OH), 3.30 (1H, d, J 13.2 Hz, CH$_A$H$_B$ pyridine), 3,59 (1H, d, J, 13.2 Hz, CH$_A$H$_B$ pyridine), 3.82 (3H, s, OMe), 4.65 (1H, br m OCH), 6.24 (1H, dd, J 3.3, 0.7 Hz, furan H$_3$), 6.35 (1H, dd, J 3.3, 1.8 Hz, furan H$_4$), 6.75–6.85 (3H, m, C$_6$H$_3$), 6.85 (2H, dd, J 4.5, 1.6 Hz, pyridine H$_3$, H$_5$), 7.43 (1H, dd, J 1.8, 0.7 Hz, furan H$_5$), and 8.33 (2H, dd, J 4.5, 1.6 Hz, pyridine H$_2$, H$_6$); m/z (ESI) 402 (M$^+$+23, 20%), 380 (M$^+$+1, 35), 287 (100), 95 (28), and 94 (97).

INTERMEDIATE 17

(3-Cyclopentyloxy-4-methoxyphenyl)-2-thienylmethanol

Thienyllithium (1.0M solution in THF; 14 ml, 14.0 mmol) was added to a solution of Intermediate 1 (3.04 g, 13.8 mmol) in THF (30 ml) at −70° C. After 0.25 h, the reaction mixture was allowed to warm to RT, stirred for 0.75 h, then quenched with 10% aqueous NH$_4$Cl solution (25 ml) and extracted with Et$_2$O (3×40 ml). The extract was dried (MgSO$_4$), concentrated in vacuo, and the orange residue subjected to chromatography (SiO$_2$; Et$_2$O/hexane, 1:1) to afford the title compound (3.88 g), as an off-white solid m.p. 79°–80° C. (from hexane-diisopropyl ether) (Found: C, 67.10; H, 6.65. C$_{17}$H$_{20}$O$_3$S requires C, 67.08; H, 6.62%); δ$_H$ (CDCl$_3$) 1.5–2.0 (8H, br m, (CH$_2$)$_4$), 2.37 (1H, br s, OH), 3.84 (3H, s, OM), 4.75 (1H, br m OCH), 5.99 (1H, br s, C HOH), 6.8–7.1 (5H, m, C$_6$H3+thiophene H$_3$, H$_4$), and 7.2–7.3 (1H, m, thiophene H$_5$) m/z (ESI) 327 (M$^+$+Na, 100%).

INTERMEDIATE 18

(3-Cyclopentyloxy-4-methoxyphenyl)-2-thienylketone

A solution of Intermediate 17 (3.37 g, 11.08 mmol) in CH$_2$Cl$_2$ (200 ml) was stirred vigorously with manganese (IV) oxide (15 g) for 2 h. The mixture was filtered through Celite® and the filtrate concentrated in vacuo to afford the title compound (3.32 g), as an amber oil (Found: C, 67.38; H, 6.08. C$_{17}$H$_{18}$O$_3$S requires C, 67.53; H, 6.00%); δ$_H$ (CDCl$_3$) 1.55–2.0 (8H, br m, (CH$_2$)$_4$), 3.93 (3H, s, OMe), 4.85 (1H, br m, OCH), 6.92 (1H, d, J 8.3 Hz, ArH ortho to OMe), 7.16 (1H, dd, 4.9, 3.8 Hz, thienyl H$_4$), 7.46 (1H, d, J 2.0 Hz, ArH ortho to cyclopentyloxy), 7.53 (1H, dd, J 8.3, 2.0 Hz ArH para to OMe), and 7.65–7.7 (2H, m, thienyl H$_3$, H$_5$); m/z (ESI) 627 (2M$^+$+Na, 90%), 325 (M$^+$+Na, 100), and 303 (M$^+$, 10).

EXAMPLE 1 a) (E) and (Z) isomers of 4-[2-(3-Cyclopentyloxy-4-methoxyphenyl)-2-phenylethenyl]pyridine Intermediate 7a (3.13 g, 8.05 mmol) was dissolved in toluene (70 ml) containing 4-toluenesulphonic acid monohydrate (1.91 g, 10.05 mmol) and the mixture heated to reflux for 1 h. The reaction mixture was poured into aqueous NaOH (10%; 100 ml) and stirred for 5 min. The mixture was extracted with Et$_2$O (3×70 ml) and the organic extract washed with water (80 ml), and brine (80 ml), then dried (MgSO$_4$), and concentrated in vacuo to afford a mixture of the title compounds (3.0 g) as a viscous pale yellow oil. δ$_H$ (CDCl$_3$) 1.5–2.1 (8H, br m, (CH$_2$)$_4$), 3.82 (major) and 3.84 (minor) (3H, s, OMe), 4.8 (1H, br m, OCHCH$_2$), 6.6–7.4 (11H, m, ArH ortho to OMe+2×ArH meta to OMe+C$_6$ H$_5$+pyridine H$_3$, H$_5$), and 8.2–8.35 (2H, m, pyridine H$_2$, H$_6$); m/z 372 (M$^+$+1, 12%), 371 (M$^+$, 40), 304 (21), 303 (100), 302 (72) and 274 (22).

The following compounds were prepared using a similar procedure:

b) (E) and (Z) isomers of 2-[2-(3-Cyclopentyloxy-4-methoxyphenyl)-2-phenylethenyl]pyrazine From Intermediate 7b (570 mg, 1.5 mmol) and 4-toluene sulphonic acid (about 20 mg). Upon completion, the reaction mixture was concentrated in vacuo then subjected to chromatography (SiO$_2$; Et$_2$O) to afford the title compound (520 mg) as a colourless oil. δ$_H$ (CDCl$_3$) 1.5–2.0 (8H, br m, (CH$_2$)$_4$), 3.84 and 3.86 (3H, s, OMe), 4.58 and 4.72 (1H, br m, OCH), 6.65–7.5 (9H, m, C$_6$H$_5$+C=CH+ArH ortho to OMe+ 2×ArH meta to OMe), 7.90 and 8.04 (1H, d, J 1.5 Hz, pyrazine H$_3$), 8.18 and 8.21 (1H, d, J 2.5 Hz, pyrazine H$_6$), and 8.45 and 8.48 (1H, m, pyrazine H$_5$).

c) (E) and (Z) isomers of 3-[2-(3-Cyclopentyloxy-4-methoxyphenyl)-2-phenylethenyl]-2-methoxypyrazine From Intermediate 10a (2.94 g, 7.0 mmol) and 4-toluenesulphonic acid (about 20 mg) as described for Intermediate 7b to afford the title compound (2.67 g) as a yellow oil. δ$_H$ (CDCl$_3$) 1.5–2.0 (8H, br m, (CH$_2$)$_4$), 3.80, 3.81, 3.83, 3.86 (2×3H, s, 2×OMe), 4.50, 4.70 (1H, br m, OCH), 6.60–7.5 (9H, m, C$_6$H$_5$+C=CH+ArH ortho to OMe+2×ArH meta to OMe) and 7.7–7.95 (2H, m, pyrazine H$_5$, H$_6$).

d) (i) (E) 4-[2-(3-Cyclopentyloxy-4-methoxyphenyl)-2-phenylethenyl]-3,5-dichloropyridine (ii) (Z) 4-[2-(3-Cyclopentyloxy-4-methoxyphenyl)-2-phenylethenyl]-3,5-dichloropyridine From Intermediate 7c (1.60 g, 3.58 mmol) and 4-toluenesulphonic acid (0.85 g). Purification by column chromatography (SiO$_2$; CH$_2$Cl$_2$) afforded: i) (E) title compound (960 mg) as an off-white solid m.p. 138.5°–140° C. δ$_H$ (CDCl$_3$) 1.5–2.0 (8H, br m, (CH$_2$)$_4$), 3.88 (3H, s, OMe), 4.72 (1H, br m, OCH), 6.59 (1H, s, C=CH), 6.85 (1H, d, J 8.4 Hz, Ar H ortho to OMe), 6.90 (1H, d, J 2.0 Hz, ArH ortho to cyclopentyloxy), 6.95 (1H, dd, J 8.4, 2.0 Hz, ArH para to cyclopentyloxy), 7.0–7.1 (2H, m, H$_2$, H$_6$ of C$_6$H$_5$), 7.15–7.3 (3H, m, H$_3$, H$_4$, H$_5$ of C$_6$H$_5$), and 8.35 (2H, s, pyridine H$_2$, H$_6$). and ii) (Z) title compound (240 mg) as an off-white solid. m.p. 155°–156.5° C. δ$_H$ (CDCl$_3$) 1.4–1.8 (8H, br m (C H$_2$)$_4$), 3.80 (3H, s, OMe), 4.42 (1H, br m OCH), 6.52 (1H, d, J 2.00 Hz, m ArH ortho to cyclopentyloxy), 6.56 (1H, s, C=CH), 6.57 (1H, dd, J 8.4, 2.0 Hz, ArH para to cyclopentyloxy), 6.68 (1H, d, J 8.4 Hz, ArH ortho to OMe), 7.3–7.45 (5H,m, C$_6$H$_5$), and 8.37 (2H, s, pyridine H$_2$, H$_6$).

e) (E) and (Z) isomers of 2-[2-(3-Cyclopentyloxy-4-methoxy phenyl)-2-phenylethenyl]-4-methylpyridine From Intermediate 10b (1.15 g, 2.85 mmol). Purification by chromatography (SiO$_2$; EtOAc) afforded the title compound (1.2 g) as a pale yellow solid; δ$_H$ (CDCl$_3$) 1.4–1.9 (8H, br m, (CH$_2$)$_4$), 2.04 (major), 2.09 (minor) (3H, s, pyridine Me), 3.85 (major), 3.88 (minor) (3H, s, OMe), 4.58 (minor), 4.72 (major) (1H, br m, OCH), 6.4–7.5 (11H, m, C$_6$ H$_5$+C$_6$H$_3$+pyridine H$_3$, H$_5$+C=CH), 8.5–8.55 (1H, m, pyridine H$_6$). $^1$Hn.m.r indicates a 2:1 E/Z ratio.

f) (E) and (Z) isomers of 4-[2-(3-Cyclopentyloxy-4-methoxy phenyl)-2-phenylethenyl]pyrimidine From Intermediate 10c (2.55 g). Purification by chromatography (SiO$_2$; Et$_2$O) afforded the title compound (1.20 g) as a pale yellow foam; δ$_H$ (CDCl$_3$) 1.5–2.0 (8H, br m, (C H$_2$)$_4$), 3.88, 3.90 (3H, s, OMe), 4.60, 4.70 (1H, br m, OC H), 6.44, 6.64 (1H, d, J 5.2 Hz, pyrimidine H$_5$), 6.65–7.0 (3H, m, C$_6$H$_3$), 7.2–7.45 (6H, m, C$_6$H$_5$+C=CH), 8.26, 8.32 (1H, d, J 5.2 Hz, pyrimidine H$_6$), and 9.10, 9.12 (1H, ca s, pyrimidine H$_2$).

g) (E) and (Z) isomers of 3-[2-(3-Cyclopentyloxy-4-methoxy phenyl)-2-phenylethenyl]pyridazine From Intermediate 10d (4.0 g). Purification by chromatography (SiO$_2$; Et$_2$O) afforded the title compound (2.07 g) as a pale yellow solid (Found: C, 77.59; H, 6.49; N, 7.24. C$_{24}$H$_{24}$N$_2$O$_2$ requires C, 77.39; H, 6.50; N, 7.52%); δ$_H$ (CDCl$_3$) 1.5–1.9 (8H, br m, (CH$_2$)$_4$), 3.88, 3.90 (3H, s, OMe), 4.58, 4.70 (1H, br m, OCH), 6.6–7.5 (11H, m, C$_6$H$_5$+C$_6$H$_3$+C=CH+pyridazine H$_4$, H$_{5+}$), and 8.85–8.90 (1H, m, pyridazine H$_6$) ($^1$Hnmr indicates a 3:2 E/Z ratio); m/z (ESI) 396 (M$^+$+1+Na, 57%), 395 (M$^+$+Na, 100), 374 (66), 373 (78), and 305 (16).

EXAMPLE 2

(E) and (Z) isomers of 4-[1-(3-Cyclopentyloxy-4-methoxyphenyl)-2-(4-pyridyl)ethenyl]pyridine A mixture of Intermediate 6 (0.48 g, 1.58 mmol), Cs$_2$CO$_3$ (0.56 g, 1.73 mmol), and cyclopentyl bromide (0.26 g, 1.743 mmol) in DMF (20 ml) was stirred at RT overnight. A further portion of Cs$_2$CO$_3$ (0.20 g, 0.61 mmol) and cyclopentyl bromide (0.28 g, 1.86 mmol) was added, the mixture stirred for 1.5h then concentrated in vacuo. The residue was subjected to chromatography (SiO$_2$; EtOAc/CH$_3$OH/Et$_3$N, 100:1:0.4) to afford the title compound (0.42 g) as a white solid. m.p. 136°–138° C. (cyclohexane); $\delta_H$ (CDCl$_3$) 1.5–2.0 (8H, br m (CH$_2$)$_4$), 3.84 (3H, s, OMe), 4.65 (1H, br m OCHCH$_2$), 6.7–6.9 (6H, m, ArH ortho to OMe+2×ArH meta to OMe+C=CH+pyridine H$_3$, H$_5$), 7.08 (2H, dd, J 4.5, 1.5 Hz, pyridine pyridine H$_3$', H$_5$'), 8.32 (2H, dm, J 5.0 Hz pyridine H$_2$, H$_6$), and 8.55 (2H, dd, J 4.5, 1.5 Hz, pyridine H$_2$', H$_6$'); m/z 372 (M$^+$28%), 305 (37), 304 (100), 303 (95), 275 (18), and 41 (18).

EXAMPLE 3 a) (E) and (Z) isomers of 4-[2-(3-Cyclopentyloxy-4-methoxy phenyl)-2-phenylethenyl] phenol A mixture of Intermediate 9 (2.94 g, 10 mmol), 4-bromophenol (2.16 g, 12.5 mmol), Et$_3$N (2.52 g, 25 mmol), tri-o-tolyl phosphine (0.06 g, 0.2 mmol) and palladium acetate (0.022 g, 0.1 mmol) was heated in a bomb at 140° C. for 16 h. Upon cooling, the reaction mixture was diluted with NH$_4$Cl (10%; 50 ml) and CH$_2$Cl$_2$ (50 ml). The organic layer was separated and the aqueous layer extracted with CH$_2$Cl$_2$ (50 ml). The combined organic layer was dried (MgSO$_4$), filtered and concentrated. Purification by column chromatography (SiO$_2$; hexane/Et$_2$O, 1:1) yielded the title compound (1:1 mixture of isomers) (0.8 g) as a yellow foam. $\delta_H$ (CDCl$_3$) 1.2–1.9 (8H, br m, (CH$_2$)$_4$), 3.81, 3.83 (3H, s, OMe), 4.59, 4.69 (1H, br m, OCH), 5.5, 5.63 (1H, br s, OH), 6.55–7.0 (8H, m, C$_6$H$_3$+C$_6$H$_4$+C=CH), and 7.15–7.35 (5H, m, C$_6$H$_5$) [N.B. $^1$Hn.m.r. indicates ca 1:1 E/Z mixture of isomers); m/z (ESI) 410 (M$^+$+1+Na, 18%), 409 (M$^+$+Na, 100) 387 (M$^+$+1, 62), 319 (38), 318 (22), 301 (19), 236 (22), and 135 (20).

The following compounds were prepared using a similar procedure:

b) (E) and (Z) isomers of 3-[2-(3-Cyclopentyloxy-4-methoxy phenyl)-2-phenylethenyl] benzoic acid From Intermediate 9 (2.94 g, 10 mmol) and 3-bromobenzoic acid (5.03 g, 25 mmol). Purification by column chromatography [SiO$_2$; 10%, CH$_3$OH/CH$_2$Cl$_2$] furnished the title compounds (2 g) as a viscous yellow oil. $\delta_H$ (CDCl$_3$) 1.45–2.0 (8H, br m, (CH$_2$)$_4$), 3.86, 3.87 (3H, s, OMe), 4.55, 4.7 (1H, br m, OCH), 6.65–8.25 (13H, m, C$_6$H$_5$+C$_6$H$_4$+C$_6$H$_3$+C=CH), (CO$_2$H not observed) [N.B. $^1$Hn.m.r. indicates ca 1:1 E/Z mixture of isomers]; m/z (ESI) 437 (M$^+$+23, 60%), 301 (67), 281 (100), and 259 (52).

c) (E) and (Z) isomers of 4-[2-(3-Cyclopentyloxy-4-methoxy phenyl)-2-phenylethenyl] anisole From Intermediate 9 (1.19 g, 4.04 mmol) and 4-bromoanisole (0.757 g, 4.05 mmol). Purification by column chromatography [SiO$_2$; hexane/Et$_2$O, 4:1] furnished the title compounds (0.78 g) as a yellow oil. $\delta_H$ (CDCl$_3$) 1.5–2.0 (8H, br m, (CH$_2$)$_4$), 3.72, 3.73 (3H, s, OMe), 3.82, 3.86 (3H, s, OMe), 4.58, 4.67 (1H, br m, OCH), 6.6–6.9 (6H, m, C$_6$H$_3$+2×ArH ortho to OMe+C=CH), 6.93, 7.00 (2H, d, J 8.5 Hz, 2×ArH meta to OMe) and 7.15–7.35 (5H, m, C$_6$H$_5$) [N.B. $^1$Hn.m.r. indicates ca 1:1 E/Z mixture of isomers]; m/z (ESI) 424 (M$^+$+1+Na, 20%), 423 (M$^+$+Na, 100%), 374 (12), 281 (20), 198 (12), 132 (12) and 86 (12).

d) (E) and (Z) isomers of Methyl 4-[2-(3-Cyclopentyloxy-4-methoxyphenyl)-2-phenylethenyl]benzoate From Intermediate 9 (2.94 g, 10 mmol) and methyl 4-bromobenzoate (2.69 g, 12.5 mmol) to afford the title compounds (3.35 g) as a yellow gum; $\delta_H$ (CDCl$_3$) 1.4–2.0 (8H, br m, (CH$_2$)$_4$), 3.86, 3.87 (6H, s, OMe+CO$_2$Me), 4.54, 4.67 (1H, br m, OCH), 6.6–7.4 (11H, m, C$_6$H$_5$+C$_6$H$_3$+C=CH+2×ArH meta to CO$_2$Me), and 7.75–7.85 (2H, m, 2×ArH ortho to CO$_2$Me) [N.B. $^1$Hn.m.r. indicates ca 1:1 E/Z mixture of isomers]; m/z (ESI) 429 (M$^+$+1+Na, 28%), 362 (18), 361 (28), 330 (70), and 329 (68).

e) (E) and (Z) isomers of 3-[2-(3-Cyclopentyloxy-4-methoxyphenyl)-2-phenylethenyl]pyridine From Intermediate 9 (1.00 g, 3.4 mmol) and 3-bromopyridine (1.28 g, 8.1 mmol). Purification by chromatography (SiO$_2$; Et$_2$O) afforded the title compound (0.50 g) as a pale yellow gum; $\delta_H$ (CDCl$_3$) 1.45–2.0 (8H, br m, (CH$_2$)$_4$), 3.85 (major), 3.87 (minor) (3H, s, OMe), 4.55 (minor), 4.69 (major) (1H, br m, OCH), 6.65–7.5 (11H, m, C$_6$H$_5$+C$_6$H$_3$+pyridine H$_4$, H$_5$+C=C), and 8.2–8.45 (2H, m, pyridine H$_2$, H$_6$).

EXAMPLE 4

(E) and (Z) isomers of 4-[2-(3-Cyclopentyloxy-4-methoxyphenyl)-2-phenylethenyl]acetoxybenzene To a stirred solution of the compound of Example 3a (0.2 g, 0.52 mmol) in CH$_2$Cl$_2$ (5 ml), under a nitrogen atmosphere, was added Et$_3$N (0.101 g, 0.14 ml, 1 mmol) followed by acetyl chloride (0.0785 g, 0.071 ml, 1 mmol). The reaction mixture was stirred at RT for 4 h then poured into saturated NaHCO$_3$ (10 ml). The organic layer was separated and the aqueous layer extracted with CH$_2$Cl$_2$. The combined organic layer was dried (MgSO$_4$), filtered, and the solvent removed in vacuo to furnish the title compounds (0.222 g) as a colourless oil. $\delta_H$ (CDCl$_3$) 1.5–1.9 (8H, br m, (CH$_2$)$_4$), 2.23, 2.24 (3H, s, OCOMe), 3.83, 3.86 (3H, s, OMe), 4.56, 4.67 (1H, br m, OCH), and 6.7–7.4 (13H, m, C$_6$H$_5$+C$_6$H$_4$+C$_6$H$_3$+C=CH)[N.B. $^1$Hn.m.r. indicates ca 1:1 E/Z mixture of isomers]; m/z (ESI) (M$^+$+Na, 100%), 319 (20), 281 (29), 191 (48), 127 (50 ) and 55 (54).

EXAMPLE 5

(E) and (Z) isomers of Methyl 3-[2-(3-cyclopentyloxy-4-methoxy phenyl)-2-phenylethenyl]benzoate To a cold (0° C.) solution of the compound of Example 3b (0.25 g, 0.6 mmol) in CH$_3$OH (20 ml) was added SOCl$_2$ (0.357 g, 0.22 ml, 3 mmol) dropwise and the reaction mixture was stirred at RT for 3 h. The solvent was evaporated in vacuo, the residue dissolved in CH$_2$Cl$_2$ (20 ml) and washed with saturated NaHCO$_3$ (20 ml). The organic phase was separated and the aqueous phase extracted with CH$_2$Cl$_2$ (20 ml). The combined organic layer was dried (MgSO$_4$), filtered and the solvent evaporated in vacuo to yield the title compound (0.215 g) as a yellow oil. $\delta_H$ (CDCl$_3$) 1.4–2.0 (8H, br m, (CH$_2$)$_4$), 3.82, 3.83, 3.84, 3.85 (6H, s, OMe+CO$_2$M), 4.54, 4.69 (1H, br m, OCH), and 6.65–7.85 (13H, m, C$_6$H$_4$+C$_6$H$_4$+C$_6$H$_3$+C=CH) [N.B. $^1$Hn.m.r. indicates ca 1:1 E/Z mixture of isomers]; m/z (ESI) 429 ( M⁺+1, 25%), 361 (22), 329 (100), 159 (12), 102 (15), and 60 (75).

EXAMPLE 6

(E) and (Z) isomers of 4-[2-(4-Aminophenyl)-2-(3-cyclopentyloxy-4-methoxyphenyl)ethenyl]pyridine Water (15 ml) and trifluoroacetic acid (10 ml) were added to Intermediate 13 (6.1 g) in $CH_2Cl_2$ (15 ml) at 0° C. and the mixture allowed to warm to RT. After 6 h, the reaction mixture was concentrated in vacuo and the residue partitioned between 10% hydrochloric acid (50 ml) and EtOAc (50 ml). The aqueous layer was separated, basified to pH 14 with 20% sodium hydroxide solution, and extracted with $CH_2Cl_2$ (3×50 ml). The extract was dried ($MgSO_4$) and concentrated in vacuo to give the crude title compound (4.2 g). A portion (0.40 g) was subjected to chromatography ($SiO_2$); EtOAc) to afford the title compound (0.29 g); $\delta_H$ ($CDCl_3$) 1.45–2.0 (8H, br m, ($CH_2)_4$), 3.80 (2H, br s, N$H_2$), 3.87, 3.90 (3H, s, OMe), 4.58, 4.70 (1H, br m, OC$H$), 6.6–7.2 (10H, $C_6H_4$+$C_6H_3$+pyridine $H_3$, $H_5$+C=C$H$), and 8.3–8.4 (2H, m, pyridine $H_2$, $H_6$); m/z (ESI) 388 (M⁺+1, 100%).

EXAMPLE 7 a) (E) and (Z) isomers of 4-[2-(4-Bromophenyl)-2-(3-cyclopentyloxy-4-methoxyphenyl)ethenyl]pyridine A solution of Intermediate 7d (7.52 g, 16.0 mmol) and triethylamine (4.05 g, 5.60 ml, 40.0 mmol) in $CH_2Cl_2$ (100 ml) was cooled to 0° C. and trifluoroacetic anhydride (3.70 g, 2.50 ml, 17.6 mmol) was added dropwise. The orange-red solution was allowed to warm to RT over 20 h then water (25 ml) was added. The mixture was extracted with $CH_2Cl_2$ and the extract was dried ($MgSO_4$), concentrated in vacuo and subjected to chromatography to give the title compound (4.73 g) as a white amorphous powder. (Found: C, 66.66; H, 5.27; N, 2.99. $C_{25}H_{24}BrNO_2$ requires C, 66.67; H, 5.37; N, 3.11%); $\delta_H$ ($CDCl_3$) 1.45–1.95 (8H, br, m, ($CH_2)_4$), 3.86, 3.88 (3H, s, OMe), 4.55, 4.70 (1H, br m, OC$H$), 6.6–6.95 (6H, m, $C_6H_3$, +pyridine $H_3$, $H_5$)+C=C$H$), 7.06, 7.21 (2H, d, J 8.4 Hz, Ar$H$ of $C_6H_4$), 7.4–7.5 (2H, m, Ar$H$ of $C_6H_4$), and 8.36 (2H, ca. d, J 6.0 Hz, pyridine $H_2$, $H_6$) (¹H n.m.r. indicates a 1:1 E/Z mixture); $v_{max}$ ($CDCl_3$) 1597, 1514, and 1251 cm⁻¹; m/z (ESI) 452 (M⁺+2+Na, 100%), 450 (M⁺+Na, 88), 384 (30) and 382 (28).

The following compound was prepared in a manner similar to compound of example 7a.

b) (Z)-4-[2-(3-Cyclopentyloxy-4-methoxyphenyl)-2-(2-furyl) ethenyl]pyridine

From the compound of Intermediate 15 (1.0 g, 2.64 mmol) in $CH_2Cl_2$ (30 ml), triethylamine (0.4 g, 0.55 ml, 3.96 mmol) and trifluoroacetic anhydride (0.61 g, 0.41 ml, 2.91 mmol). Work up [includes treatment with 10% NaOH solution (25 ml)] and chromatography ($SiO_2$; EtOAc/hexane, 7:3) afforded the title compound (0.78 g) as a pale pink solid m.p. 122°–123° C.; (Found: C, 76.37; H, 6.46; N, 3.85. $C_{23}H_{43}NO_3$ requires C, 76.43; H, 6.41; N, 3.88%); $\delta_H$ ($CDCl_3$) 1.45–1.9 (8H, br m, ($CH_2)_4$), 3.90 (3H, s, OMe), 4.65 (1H, br m, OC$H$), 6.07 (1H, d, J 3.3 Hz, furan $H_3$), 6.41 (1H, dd, J 3.3, 1.8 Hz, furan $H_4$), 6.75–6.9 (5H, m, $C_6H_3$+pyridine $H_3$, $H_5$), 7.03 (1H, s, C=C$H$), 7.49 (1H, d, J 1.6 Hz, furan $H_5$), and 8.33 (2H, ca. d, J 4.6 Hz, pyridine $H_2$, $H_6$); m/z (ESI) 362 (M⁺+1, 100%), 294 (45).

EXAMPLE 8

(E) and (Z) isomers of -4-[-1-(3-Cyclopentyloxy-4-methoxyphenyl)-2-(4-pyridyl)ethenyl]benzoic acid hydrochloride Intermediate 15 (4.25 gm 8.8 mmol) in 10% aqueous HCl (15 ml) was heated to reflux for 20 min. Aqueous NaOH solution (5M; 20 ml) and EtOH (15 ml) were then added and heating continued for a further 2 h. The reaction was cooled to RT and acidified to pH 1 with 10% aqueous HCl. The mixture was extracted with $CHCl_3$ (10×100 ml), the organic extract was dried ($MgSO_4$) and concentrated in vacuo to give the title compound (2.83 g) as a yellow solid; $\delta_H$ ($d_4$-MeOH) 1.45, 1.8 (8H, br m, ($CH_2)_4$), 3.86, 3.88 (3H, s, OMe), 4.66, 4.74 (1H, br m, OC$H$), 6.65–7.65 (8H, m, C=C$H$+$C_6H_3$+pyridine $H_3$, $H_5$, +Ar$H$ meta to $CO_2H$), 8.05, 8.13 (2H, d, J ca 0.8 Hz, Ar$H$ ortho to $CO_2H$), and 8.46, 8.55 (2H, d, J ca. 6 Hz, pyridine $H_2$, $H_6$) (N.B. $CO_2H$ and $HCl$ not observed) (2H, d, J 8.2 Hz, Ar$H$); $v_{max}$ (Nujol) 1710, and 1633 cm⁻¹; m/z (ESI) 416 (M⁺+1, 100%).

EXAMPLE 9

(E) and (Z) isomers of t-Butyl N-{4-[1-(3-cyclopentyloxy-4-methoxyphenyl)-2-(4-pyridyl)ethenyl]phenyl}carbamate A mixture of diphenyl phosphoryl azide (0.61 g, 0.48 ml, 2.2 mmol), Intermediate 14 (1.00 g, 2.2 mmol), triethylamine (0.49, 0.68 ml, 4.9 mmol) and t-butanol (25 ml) was heated to reflux for 20 h. The mixture was concentrated in vacuo and the resulting brown oil partitioned between $CH_2Cl_2$ (30 ml) and 5% citric acid solution (30 ml). The organic layer was separated, washed with water (20 ml), $NaHCO_3$ solution (20 ml), and brine (20 ml), then dried ($MgSO_4$) and concentrated in vacuo to give a red oil; which was subjected to chromatography to give the title compound. (0.60 g, 56%) as a yellow foamy solid. $\delta_H$ ($CDCl_3$) 1.52, 1.54 (9H, s, C$Me_3$), 1.65–1.9 (8H, br m, ($CH_2)_4$), 3.86, 3.89 (3H, s, OMe), 4.56, 4.70 (1H, m, OC$H$), 6.6–7.4 (11H, m, Ar$H$+C=C$H$+NCO), and 8.34 (2H, d, J 5.2 Hz, pyridine $H_2$, $H_6$). (¹H n.m.r. indicates ca. 1:1 mixture of isomers); $v_{max}$ ($CHCl_3$) 3441, 1730, 1596, 1518 and 1157 cm⁻¹; m/z (ESI) 487 (M⁺+1, 75%), 472 (12), and 431 (100).

The activity and selectivity of compounds according to the invention was demonstrated in the following tests.

1. Isolated Enzyme

The potency and selectivity of the compounds of the invention was determined using a battery of distinct PDE isoenzymes as follows:

PDE I, rabbit heart
PDE II, rabbit heart
PDE III, rabbit heart
PDE IV, HL60 cells
PDE V, HL60 cells The enzymes were purified to kinetic homogeneity using standard chromatographic techniques.

Phosphodiesterase activity was assayed as follows. The reaction was conducted in 150 μl of standard mixture containing (final concentrations): 50 mM TES-NaOH buffer (pH 7.5), 10 mM $MgCl_2$, 0.1 μM [³H]-cAMP and vehicle or various concentrations of the test compounds. The reaction was initiated by addition of enzyme and conducted at 30° C. for between 5 to 30 min. The reaction was terminated by addition of 50 μl 2% trifluoroacetic acid containing [¹⁴C]-5'AMP for determining recovery of the product. An aliquot of the sample was then applied to a column of neutral alumina and the [³H]-cAMP eluted with 10 ml 0.1 TES-NaOH buffer (pH 8). The [³H]-5'AMP product was eluted with 2 ml 2M NaOH into a scintillation vial containing 10 ml of scintillation cocktail. Recovery of [³H]-5'AMP was determined using the [¹⁴C]-5'AMP and all assays were conducted in the linear range of the reaction.

A gene encoding human PDE IV has been cloned from human monocytes (Livi, et al., 1990, *Molecular and Cellular Biology*, 10, 2678). Using similar procedures we have cloned human PDE IV genes from a number of sources including eosinophils, neutrophils, lymphocytes, monocytes, brain and neuronal tissues. These genes have been transfected into yeast using an inducible vector and various recombinant proteins have been expressed which have the biochemical characteristics of PDE IV (Beavo and Reifsnyder, 1990, *TIPS*, 11, 150). These recombinant enzymes, particularly the human eosinophil recombinant PDE IV, have been used as the basis of a screen for potent, selective PDE IV inhibitors.

Compounds, according to the invention, cause a concentration-dependent inhibition of recombinant PDE IV at 0.1–1000 nM with little or no activity against PDE I, II, III or V at concentrations up to 100 μM.

2. The Elevation of cAMP in Leukocytes

The effect of compounds of the invention on intracellular cAMP was investigated using human neutrophils or guinea pig eosinophils. Human neutrophils were separated from peripheral blood, incubated with dihydrocytochalasin B and the test compound for 10 min and then stimulated with FMLP. Guinea pig eosinophils were harvested by peritoneal lavage of animals previously treated with intraperitoneal injections of human serum. Eosinophils were separated from the peritoneal exudate and incubated with isoprenaline and test compound. With both cell types, suspensions were centrifuged at the end of the incubation, the cell pellets were resuspended in buffer and boiled for 10 min prior to measurement of cAMP by specific radioimmunoassay (DuPont).

The most potent compounds induced a concentration-dependent elevation of cAMP in neutrophils and/or eosinophils at concentrations of 0.1 nM to 1 μM.

3. Suppression of Leukocyte Function

Compounds of the invention were investigated for their effects on superoxide generation and chemotaxis of human neutrophils. Neutrophils were separated from peripheral blood, incubated with dihydrocytochalasin B for superoxide generation only and test compound prior to stimulation with FMLP. The most potent compounds caused a concentration-dependent inhibition of superoxide generation and chemotaxis at concentrations of 0.1 nM to 1 μM.

Lipopolysaccharide (LPS)-induced synthesis of tumour necrosis factor (TNF) by human peripheral blood monocytes (PBM) is inhibited by compounds of the invention at concentrations of 0.01 nM to 10 μM.

4. Relaxation of Constricted Airway Smooth Muscle in vitro

The effects of compounds of the invention on guinea-pig isolated tracheal smooth muscle were investigated. Isolated tracheal rings were suspended in organ baths and immersed in oxygenated Krebs' solution. The smooth muscle was contracted with sub-maximal concentrations of histamine or carbachol prior to the addition of increasing concentrations of test compound to the organ baths. The most potent compounds caused a concentration-dependent reversal of both histamine and carbachol-induced contractions at concentrations of 1 nM to 100 μM. The compounds were generally more potent in reversing histamine-induced tone than carbachol-induced tone.

5. Effects on Cardiac Muscle in vitro

Compounds of the invention have been tested for their effects on isolated cardiac muscle. Right atrial and papillary muscles were dissected out from the hearts of guinea pigs and suspended in organ baths for measuring the rate (chronotropic) of spontaneously beating atria and force (inotropic) of the electrically stimulated papillary muscle. In these preparations, selective PDE IV inhibitors such as rolipram do not have any direct effects whereas selective PDE III inhibitors such as milrinone have positive chronotropic and inotropic effects. The non-specific PDE inhibitor theophylline, which is used in asthma as a bronchodilator, also causes significant cardiovascular changes such as tachycardia. Selective PDE IV inhibitors have advantage over theophylline, therefore, through reduced cardiovascular side effects. The most potent and selective compounds of the invention had no direct effects on the atrial and papillary muscles in vitro at concentrations up to 10 μM but in combination with PDE III inhibitors, these inhibitors showed an enhancement of chronotropic and inotropic activity, typical of selective type IV inhibitors.

6. Anti-inflammatory Activity in vivo

Interleukin-5 (IL-5)-induced pleural eosinophilia in the rat (Lisle, et al, 1993, *Br. J. Pharmacol.* 108, 230p) is inhibited by compounds of the invention given orally at doses of 0.0001 to 10.0 mg/kg. The most potent compounds cause a dose-dependent reduction in migrating eosinophils with $ED_{50}$s of 0.003 to 0.03 mg/kg p.o.

Compounds of the invention also reduce the inflammatory responses induced in rats by platelet activating factor (PAR).

7. Anti-allergic Activity in vivo

Compounds of the invention have been tested for effects on an IgE-mediated allergic pulmonary inflammation induced by inhalation of antigen by sensitised guinea pigs. Guinea pigs were initially sensitised to ovalbumin under mild cyclophosphamide-induced immunosuppression, by intraperitoneal injection of antigen in combinations with aluminium hydroxide and pertussis vaccine. Booster doses of antigen were given two and four weeks later and at six weeks, animals were challenged with aerosolised ovalbumin whilst under cover of an intraperitoneally administered anti-histamine agent (mepyramine). After a further 48 h, bronchial alveolar lavages (BAL) were performed and the numbers of eosinophils and other leukocytes in the BAL fluids were counted. The lungs were also removed for histological examination for inflammatory damage. Administration of compounds of the invention (0.001–10 mg/kg i.p. or p.o.), up to three times during the 48 h following antigen challenge, lead to a significant reduction in the eosinophilia and the accumulation of other inflammatory leukocytes. There was also less inflammatory damage in the lungs of animals treated with compounds of the invention.

8. Effects on Pulmonary Dynamics

Compounds of the invention have been tested for their effects on ozone-induced hyperreactivity of the airways of guinea pigs. Following the inhalation of ozone, guinea pigs become very much mere sensitive to the bronchoconstrictor effects of inhaled histamine than naive animals (Yeadan et al, 1992, *Pulmonary Pharm.*, 5, 39). There is a pronounced shift to the left (10–30 fold) of the dose response curve to histamine and a highly significant increase in the maximum increase in pulmonary resistance. Compounds of the invention administered 1 h prior to ozone by the intraperitoneal or oral (0.001–10 mg/kg) route caused a dose-dependent inhibition of ozone-induced hyperreactivity.

Compounds of the invention are free from adverse effects following repeated overdosage to rats or dogs. For example, oral administration of 125 mg/kg/day of active compounds to rats for 30 days is not associated with adverse toxicity.

We claim:
1. A compound of formula (1)

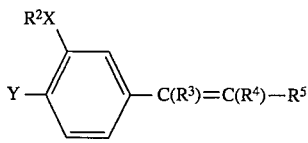

wherein

Y represents a halogen atom or a group —OR$^1$, where R$^1$ is an C$_{1-6}$alkyl group optionally substituted by one or more halogen atoms;

X is —O—, —S— or —N(R$^6$)—, where R$^6$ is a hydrogen atom or an C$_{1-6}$alkyl group;

R$^2$ is a C$_{3-8}$cycloalkyl or C$_{3-8}$cycloalkenyl group optionally substituted by one, two or three substituents selected from the group consisting of halogen, C$_{1-6}$alkyl, hydroxyl, and C$_{1-6}$alkoxy;

R$^3$ and R$^4$, which may be the same or different, is each a group —(CH$_2$)$_n$Ar, where n is zero or an integer 1, 2 or 3, and Ar is a monocyclic or bicyclic C$_{6-12}$aryl group, or a monocyclic or bicyclic heteroaryl group which is a member selected from the group consisting of pyrrolyl, furyl, thienyl, imidazolyl, N-methylimidazolyl, N-ethylimidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, pyridyl, pyrimidinyl, pyridazinyl, pyrazinyl, 1,3,5-triazinyl, 1,2,4-triazinyl, 1,2,3-triazinyl, benzofuryl, isobenzofuryl, benzothienyl, isobenzothienyl, indolyl, isoindolyl, benzimidazolyl, benzothiazolyl, benzoxazolyl, quinazolinyl, naphthyridinyl, pyrido[3,4-b]pyridyl, pyrido[3,2-b]pyridyl, pyrido[4,3-b]pyridyl, quinolinyl, isoquinolinyl, tetrazolyl, 5,6,7,8-tetrahydroquinolinyl and 5,6,7,8-tetrahydroisoquinolinyl;

and wherein the aryl and heteroaryl groups defining R$^3$ and R$^4$ are optionally substituted by one, two, three or more substituents selected from the group consisting of an atom or group R$^8$ or —Alk$^1$(R$^8$)$_m$ wherein R$^8$ is a halogen atom, or an amino (—NH$_2$), substituted amino, nitro, cyano, hydroxyl (—OH), substituted hydroxyl, cycloalkoxy, formyl [HC(O)—], carboxyl (—CO$_2$H), esterified carboxyl, thiol (—SH), substituted thiol, —C(O)Alk$^1$, —SO$_3$H, —SO$_2$Alk$^1$, —SO$_2$NH$_2$, —SO$_2$NHAlk$^1$, —SO$_2$N[Alk$^1$]$_2$, —CONH$_2$, —CONHAlk$^1$, C—ON[Alk$^1$]$_2$, —NHSO$_2$H, —NHSO$_2$Alk$^1$, —N[SO$_2$Alk$^1$]$_2$, —NHSO$_2$NH$_2$, —NHSO$_2$NHAlk$^1$, —NHSO$_2$N[Alk$^1$]$_2$, —NHC(O)Alk$^1$, or —NHC(O)OAlk$^1$ group; Alk$^1$ is a straight or branched C$_{1-6}$alkylene, C$_{2-6}$alkenylene, or C$_{2-6}$alkynylene chain optionally interrupted by one, two, or three —O—, or —S— atoms or —S(O)p—, where p is an integer 1 or 2, or —N(R$^6$)— as defined above; and m is zero or an integer 1, 2 or 3; and R$^5$ is a hydrogen atom or an C$_{1-6}$alkyl group optionally substituted by one, two or three substituents selected from the group consisting of halogen, hydroxyl, and C$_{1-6}$alkoxy;

or a salt, solvate, hydrate or N-oxide thereof.

2. A compound according to claim 1 wherein X is —O—.

3. A compound according to claim 1 or claim 2, wherein Y is a group —OR$^1$ where R$^1$ is a methyl group.

4. A compound according to claim 1 wherein R$^2$ is a cyclopentyl group.

5. A compound according to claim 1 wherein Y is a —OCH$_3$ group, X is —O—, R$^2$ is a cyclopentyl group and wherein R$^3$ and R$^4$ is each independently a group —Ar.

6. A compound according to claim 5 wherein R$^3$ is a group Ar where Ar is an unsubstituted or substituted monocyclic aryl or monocyclic nitrogen-containing heteroaryl group and R$^4$ is a group Ar where Ar is an unsubstituted or substituted monocyclic nitrogen-containing heteroaryl group.

7. A compound according claim 6 wherein the monocyclic aryl group is an unsubstituted or substituted phenyl group, the monocyclic heteroaryl group is an unsubstituted or substituted furyl or thienyl group and the monocyclic nitrogen-containing heteroaryl group is an unsubstituted or substituted pyridyl, pyridazinyl, pyrimidinyl or pyrazinyl group.

8. A compound according to claim 7 wherein the nitrogen-containing heteroaryl group is a substituted or unsubstituted pyridyl group.

9. A compound according to claim 1 selected from the (E) and (Z) isomers of:

4-[2-(3-Cyclopentyloxy-4-methoxyphenyl)-2-(2-furyl) ethenyl]pyridine;

4-[2-(3-Cyclopentyloxy-4-methoxyphenyl)-2-(2-thienyl)ethenyl]pyridine;

4-[2-(3-Cyclopentyloxy-4-methoxyphenyl)-2-phenylethenyl]-3-methylimidazole;

4-[2-(3-Cyclopentyloxy-4-methoxyphenyl)-2-phenylethenyl]pyridine;

4-[1-(3-Cyclopentyloxy-4-methoxyphenyl)-2-(4-pyridyl)ethenyl]pyridine;

(4-[2-(3-Cyclopentyloxy-4-methoxyphenyl)-2-(4-fluorophenylethenyl]pyridine;

4-[2-(3-Cyclopentyloxy-4-methoxyphenyl)-2-(4-trifluoromethylphenyl)ethenyl]pyridine;

4-[2-(3-Cyclopentyloxy-4-methoxyphenyl)-2-(2-methoxyphenylethenyl))pyridine;

4-[2-(3-Cyclopentyloxy-4-methoxyphenyl)-2-(4-methoxyphenyl)ethenyl]pyridine;

4-[2-(3-Cyclopentyloxy-4-methoxyphenyl)-2-(4-methylphenyl) ethenyl]pyridine;

4-[2-(3-Cyclopentyloxy-4-methoxyphenyl)-2-(3-methylphenyl)ethenyl]pyridine;

4-[2-(3-Cyclopentyloxy-4-methoxyphenyl)-2-(3-cyclopentyloxy-4-methoxyphenyl)ethenyl]pyridine;

4-[2-(3-Cyclopentyloxy-4-methoxyphenyl)-2-phenylethenyl]-3,5-dichloropyridine;

2-[2-(3-Cyclopentyloxy-4-methoxyphenyl)-2-phenylethenyl]pyridine;

4-[1-(3-Cyclopentyloxy-4-methoxyphenyl)-2-(4-pyridyl)ethenyl]aniline;

4-[1-(3-Cyclopenxyloxy-4-methoxyphenyl0-2-(4-pyridyl)ethenyl]benzoic acid;

Ethyl N-{4-[1-(3-Cyclopentyloxy-4-methoxyphenyl)-2-(4-pyridyl) ethenyl]phenyl}carbamate;

N-{4-[1-(3-Cyclopentyloxy-4-methoxyphenyl)-2(4-pyridyl)ethenyl]phenyl}N'-ethylurea;

N-{4-[1-(3-Cyclopentyloxy-4-methoxyphenyl)]-2-(4-pyridyl)ethenyl}phenylacetamide;

3-[2-(3-Cyclopentyloxy-4-methoxyphenyl)-2-phenylethenyl]pyridine;

4-[2-2(3-Cyclopentyloxy-4-methoxyphenyl)-2-phenylethenyl]pyrimidine;

4-[2-(3-Cyclopentyloxy-4-methoxyphenyl)-2-(4-hydroxymethylphenyl)ethenyl]pyridine;

4-[1-(3-Cyclopentyloxy-4-methoxyphenyl)-2-(4-pyridyl)ethenyl]benzamide;

Ethyl-4-[1-(3-Cyclopentyloxy-4-methoxyphenyl)-2-(4-phenylethenyl]benzoate;

N-{4-[1-(3-Cyclopentyloxy-4-methoxyphenyl)-2-(4-pyridyl)ethenyl]phenyl}methanesulphonamide; or each enantiomer thereof; and the salts, solvates, hydrate and N-oxides thereof.

10. A pharmaceutical composition comprising a compound of formula (1)

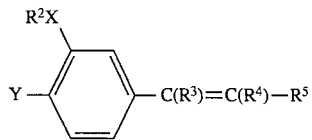

wherein

Y represents a halogen atom or a group —OR$^1$, where R$^1$ is an C$_{1-6}$alkyl group optionally substituted by one or more halogen atoms;

X is —O—, —S— or —N(R$^6$)—, where R$^6$ is a hydrogen atom or an C$_{1-6}$alkyl group;

R$^2$ is a C$_{3-8}$cycloalkyl or C$_{3-8}$cycloalkenyl group optionally substituted by one, two or three substituents selected from the group consisting of halogen, C$_{1-6}$alkyl, hydroxyl, and C$_{1-6}$alkoxy;

R$^3$ and R$^4$, which may be the same or different, is each a group —(CH$_2$)$_n$Ar, where n is zero or an integer 1, 2 or 3, and Ar is a monocyclic or bicyclic C$_{6-12}$aryl group, or a monocyclic or bicyclic heteroaryl group which is a member selected from the group consisting of pyrrolyl, furyl, thienyl, imidazolyl, N-methylimidazolyl, N-ethylimidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, pyridyl, pyrimidinyl, pyridazinyl, pyrazinyl, 1,3,5-triazinyl, 1,2,4-triazinyl, 1,2,3-triazinyl, benzofuryl, isobenzofuryl, benzothienyl, isobenzothienyl, indolyl, isoindolyl, benzimidazolyl, benzothiazolyl, benzoxazolyl, quinazolinyl, naphthyridinyl, pyrido[3,4-b]pyridyl, pyrido[3,2-b]pyridyl, pyrido[4,3-b]pyridyl, quinolinyl, isoquinolinyl, tetrazolyl, 5,6,7,8-tetrahydroquinolinyl and 5,6,7,8-tetrahydroisoquinolinyl;

and wherein the aryl and heteroaryl groups defining R$^3$ and R$^4$ are optionally substituted by one, two, three or more substituents selected from the group consisting of an atom or group R$^8$ or —Alk$^1$(R$^8$)$_m$ wherein R$^8$ is a halogen atom, or an amino (—NH$_2$), substituted amino, nitro, cyano, hydroxyl (—OH), substituted hydroxyl, cycloalkoxy, formyl [HC(O)—], carboxyl (—CO$_2$H), esterified carboxyl, thiol (—SH), substituted thiol, —C(O)Alk$^1$, —SO$_3$H, —SO$_2$Alk$^1$, —SO$_2$NH$_2$, —SO$_2$NHAlk$^1$, —SO$_2$N[Alk$^1$]$_2$, —CONH$_2$, —CONHAlk$^1$, C—ON[Alk$^1$]$_2$, —NHSO$_2$H, —NHSO$_2$Alk$^1$, —N[SO$_2$Alk$^1$]$_2$, —NHSO$_2$NH$_2$, —NHSO$_2$NHAlk$^1$, —NHSO$_2$N[Alk$^1$]$_2$, —NHC(O)Alk$^1$, or —NHC(O)OAlk$^1$ group; Alk$^1$ is a straight or branched C$_{1-6}$alkylene, C$_{2-6}$alkenylene, or C$_{2-6}$alkynylene chain optionally interrupted by one, two, or three —O—, or —S— atoms or —S(O)p—, where p is an integer 1 or 2, or —N(R$^6$)— as defined above; and m is zero or an integer 1, 2 or 3; and R$^5$ is a hydrogen atom or an C$_{1-6}$alkyl group optionally substituted by one, two or three substituents selected from the group consisting of halogen, hydroxyl, and C$_{1-6}$alkoxy;

or a salt, solvate, hydrate or N-oxide thereof;
together with one or more pharmaceutically acceptable carriers, excipients or diluents.

11. A method of preventing or treating an inflammatory disease by means of the therapeutic effect achieved by elevating the intra-cellular levels of adenosine 3',5'-cyclic monophosphate (cAMP) within inflammatory leukocytes of a patient suffering from such an inflammatory disease, comprising the step of administering to said patient an amount of a selective inhibitor of one or more of the phosphodiesterase (PDE) IV family of isoenzymes, which is sufficient to obtain said therapeutic effect, said inhibitor being one or more compounds of the formula:

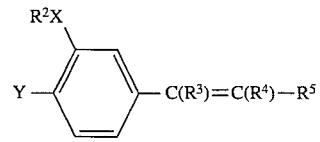

wherein

Y represents a halogen atom or a group —OR$^1$, where R$^1$ is an C$_{1-6}$alkyl group optionally substituted by one or more halogen atoms;

X is —O—, —S— or —N(R$^6$)—, where R$^6$ is a hydrogen atom or an C$_{1-6}$alkyl group;

R$^2$ is a C$_{3-8}$cycloalkyl or C$_{3-8}$cycloalkenyl group optionally substituted by one, two or three substituents selected from the group consisting of halogen, C$_{1-6}$alkyl, hydroxyl, and C$_{1-6}$alkoxy;

R$^3$ and R$^4$, which may be the same or different, is each a group —(CH$_2$)$_n$Ar, where n is zero or an integer 1, 2 or 3, and Ar is a monocyclic or bicyclic C$_{6-12}$aryl group, or a monocyclic or bicyclic heteroaryl group which is a member selected from the group consisting of pyrrolyl, furyl, thienyl, imidazolyl, N-methylimidazolyl, N-ethylimidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, pyridyl, pyrimidinyl, pyridazinyl, pyrazinyl, 1,3,5-triazinyl, 1,2,4-triazinyl, 1,2,3-triazinyl, benzofuryl, isobenzofuryl, benzothienyl, isobenzothienyl, indolyl, isoindolyl, benzimidazolyl, benzothiazolyl, benzoxazolyl, quinazolinyl, naphthyridinyl, pyrido[3,4-b]pyridyl, pyrido[3,2-b]pyridyl, pyrido[4,3-b]pyridyl, quinolinyl, isoquinolinyl, tetrazolyl, 5,6,7,8-tetrahydroquinolinyl and 5,6,7,8-tetrahydroisoquinolinyl;

and wherein the aryl and heteroaryl groups defining R$^3$ and R$^4$ are optionally substituted by one, two, three or more substituents selected from the group consisting of an atom or group R$^8$ or —Alk$^1$(R$^8$)$_m$, wherein R$^8$ is a halogen atom, or an amino (—NH$_2$), substituted amino, nitro, cyano, hydroxyl (—OH), substituted hydroxyl, cycloalkoxy, formyl [HC(O)—], carboxyl (—CO$_2$H), esterified carboxyl, thiol (—SH), substituted thiol, —C(O)Alk$^1$, —SO$_3$H, —SO$_2$Alk$^1$, —SO$_2$NH$_2$, —SO$_2$NHAlk$^1$, —SO$_2$N[Alk$^1$]$_2$, —CONH$_2$, —CONHAlk$^1$, C—ON[Alk$^1$]$_2$, —NHSO$_2$H, —NHSO$_2$Alk$^1$, —N[SO$_2$Alk$^1$]$_2$, —NHSO$_2$NH$_2$, —NHSO$_2$NHAlk$^1$, —NHSO$_2$N[Alk$^1$]$_2$, —NHC(O)Alk$^1$, or —NHC(O)OAlk$^1$ group; Alk$^1$ is a straight or branched C$_{1-6}$alkylene, C$_{2-6}$alkenylene, or C$_{2-6}$alkynylene chain optionally interrupted by one, two, or three —O—, or —S— atoms or —S(O)p—, where p is an integer 1 or 2, or —N(R$^6$)— as defined above; and m is zero or an integer 1, 2 or 3; and R$^5$ is a hydrogen atom or an C$_{1-6}$alkyl group optionally substituted by one, two or three substituents selected from the group consisting of halogen, hydroxyl, and C$_{1-6}$alkoxy;

or a salt, solvate, hydrate or N-oxide thereof.

12. A method according to claim 11 wherein the inflammatory disease is asthma and the therapeutic effect which is achieved is both an anti-inflammatory effect and a bronchodilator effect.

13. A method according to claim 11 wherein the inflammatory disease is one or more members selected from the group essentially consisting of inflammatory airway disease, chronic bronchitis, eosinophilic granuloma, inflammatory arthritis, atopic dermatitis, urticaria, allergic rhinitis, adult respiratory distress syndrome, and allergic conjunctivitis.

14. A method according to claim 11 wherein the therapeutically effective amount of the selective inhibitor is in the range of from about 100 ng to 100 mg per kg of body weight of the patient being treated.

* * * * *

UNITED STATES PATENT AND TRADEMARK OFFICE
CERTIFICATE OF CORRECTION

PATENT NO. : 5,580,888            Page 1 of 2
DATED     : December 3, 1996
INVENTOR(S) : Warrellow et al.

It is certified that error appears in the above-indentified patent and that said Letters Patent is hereby corrected as shown below:

Column 3, line 58, delete "13" and insert a --,--

Column 4, line 51, delete "$^{u}_{6}$ alkylamino" and insert --$C_1$-$_6$ alkylamino-- therefor.

Column 4, line 61, delete "thio$C_{1-6}$alkyl" and insert - - thio$C_{1-6}$alkyl - - therefor.

Column 6, line 64, insert a hyphen between "2" and "thie".

Column 7, line 25, delete "4-[1-(3-Cyclopenxyloxy-4-methoxyphenyl0-2-(4-py-" and insert --4-[1-(3-Cyclopentyloxy-4-methoxyphenyl]-2-(4-py--- therefor.

Column 12, line 37, delete "in" and insert --In-- therefor.

Column 16, line 32, delete "(150 ml)" and insert --(250 ml)-- therefor.

Column 16, line 63, delete "(2>100ml)" and insert --(2x100ml)-- therefor.

Column 20, line 50, delete "3,5-Dichldropyridine" and insert --3,5-Dichloropyridine-- therefor.

Column 21, line 22, after "236" insert --(10).--.

UNITED STATES PATENT AND TRADEMARK OFFICE
CERTIFICATE OF CORRECTION

PATENT NO. : 5,580,888
DATED : December 3, 1996
INVENTOR(S) : Warrellow et al.

It is certified that error appears in the above-indentified patent and that said Letters Patent is hereby corrected as shown below:

Column 23, line 25, delete "$C_6H3$" and insert --$C_6\underline{H}_3$- therefor.

Column 24, line 37, delete "2.00 Hz," and insert --2.0 OHz,-- therefor.

Column 26, line 66, delete "$C_6H_4$" and insert --$C_6\underline{H}_5$-- therefor.

Column 27, line 6, delete "pentyioxy" and insert --pentyloxy-- therefor.

Column 30, line 54, delete "Yeadan" and insert --Yeadon-- therefor.

Column 32, line 16, claim 9, delete "cyclopentyioxy" and insert --cyclopentyloxy-- therefor.

Signed and Sealed this

Twenty-first Day of September, 1999

Attest:

Q. TODD DICKINSON

*Attesting Officer*    *Acting Commissioner of Patents and Trademarks*